(12) United States Patent
Reeves et al.

(10) Patent No.: US 7,289,196 B2
(45) Date of Patent: Oct. 30, 2007

(54) METHOD AND APPARATUS FOR DETERMINING THE VIABILITY OF EGGS

(75) Inventors: Sidney James Reeves, Rose in Valley, Lower Hugus Road, Three Milestone, Truro (GB) TR3 6BD; Keith Angus Simpson, Torquay (GB)

(73) Assignee: Sidney James Reeves, Cornwall (GB)

( * ) Notice: Subject to any disclaimer, the term of this patent is extended or adjusted under 35 U.S.C. 154(b) by 288 days.

(21) Appl. No.: 11/072,869

(22) Filed: Mar. 4, 2005

(65) Prior Publication Data

US 2005/0206876 A1    Sep. 22, 2005

Related U.S. Application Data

(63) Continuation of application No. PCT/GB03/03869, filed on Sep. 4, 2003, and a continuation-in-part of application No. 10/475,229, filed as application No. PCT/GB02/01784 on Apr. 17, 2002, now Pat. No. 7,154,594.

(30) Foreign Application Priority Data

Apr. 20, 2001 (GB) ................... 0109765.8
Sep. 4, 2002 (GB) ................... 0220553.2

(51) Int. Cl.
*A01K 43/00* (2006.01)
(52) U.S. Cl. .......................... 356/52; 356/53
(58) Field of Classification Search ........... 356/52–68; 209/510–511
See application file for complete search history.

(56) References Cited

U.S. PATENT DOCUMENTS 3,540,824 A    11/1970    Fonda et al.
4,037,151 A    7/1977    Takeuchi
4,955,728 A    9/1990    Hebrank (Continued)

FOREIGN PATENT DOCUMENTS

FR    2455282    11/1980

(Continued)

OTHER PUBLICATIONS

"Welcome to Buddy", XP-002222494.

(Continued)

*Primary Examiner*—Gregory J. Toatley, Jr.
*Assistant Examiner*—Tri Ton
(74) *Attorney, Agent, or Firm*—Anthony R. Barkume, P.C.

(57) ABSTRACT

Determining the viability of an egg by:
(a) causing electromagnetic radiation, having one or more wavelengths in the infra-red part of the spectrum, to impinge upon the egg;
(b) receiving at least a part of the infra-red radiation that has passed through the egg and generating an output signal representative of the received infra-red radiation; and
(c) processing said output signal to determine whether there is a cyclical variation in the intensity of the infra-red radiation leaving the egg corresponding to action of a heart, the existence of said cyclical variation indicating that the egg is viable;
wherein step (a) is performed by directing infra-red radiation so that it passes through the shell for reflection from an outer surface of a vascular structure adjacent an inner surface of said shell, and step (b) is performed by receiving any infra-red radiation so reflected.

36 Claims, 15 Drawing Sheets

U.S. PATENT DOCUMENTS

| | | | |
|---|---|---|---|
| 5,173,737 A | 12/1992 | Mitchell et al. | |
| 5,504,572 A | 4/1996 | Taylor et al. | |
| 5,745,228 A | 4/1998 | Hebrank et al. | |
| 5,853,372 A | 12/1998 | Britton | |
| 6,234,320 B1 | 5/2001 | Hebrank | |
| 7,154,594 B2 * | 12/2006 | Reeves et al. | 356/52 |
| 2002/0075476 A1 * | 6/2002 | Chalker et al. | 356/53 |

FOREIGN PATENT DOCUMENTS

| | | |
|---|---|---|
| JP | 09127096 | 5/1997 |
| JP | 2001041882 A | 7/1999 |
| JP | 2001-013065 | 1/2001 |
| SU | 1597173 A1 | 10/1990 |
| WO | WO98/14781 | 4/1998 |
| WO | WO02/086495 A2 | 10/2002 |

OTHER PUBLICATIONS

PCT Written Opinion for PCT/GB03/03869.
Response to Written Opinion dated Aug. 25, 2004 for PCT/GB03/03869.
Supplemental Amendment dated Dec. 24, 2004 for PCT/GB03/03869.
PCT IPER for PCT/GB03/03869 dated Jan. 5, 2005.
PCT Search Report.
UK Search Report, Nov. 4, 2002.

* cited by examiner

NON-VIABLE

HEALTHY

POOR SIGNAL

METHOD AND APPARATUS FOR DETERMINING THE VIABILITY OF EGGS

CROSS-REFERENCE TO RELATED APPLICATIONS

This application is a continuation application of International Patent Application No. PCT/GB2003/003869, filed on Sep. 4, 2003, which claims priority from UK Patent Application No. 0220553.2 filed on Sep. 4, 2002. This application is also a continuation-in-part application of U.S. application Ser. No. 10/475,229, which entered the national stage in the United States on Oct. 17, 2003 now U.S. Pat. No. 7,154,594 based on International Application No. PCT/GB02/01784 filed on Apr. 17, 2002, which claims priority from UK Patent Application No. 0109765.8 filed on Apr. 20, 2001.

FIELD OF INVENTION

The present invention relates to a method and apparatus for determining the viability of eggs laid by egg-laying animals, and in particular but not exclusively, to eggs laid by reptiles and birds, for example parrots or poultry, to a method of vaccinating eggs in ovo, to a method of sorting eggs by gender, to an apparatus for determining the viability of a plurality of eggs, to an apparatus for sorting a plurality of eggs by viability, to a replacement part for use with the apparatus, to a computer program for use in the method, to a method of producing chickens, and to a method of propagating a vaccine.

BACKGROUND

Once an egg has been laid by an animal, it must undergo a period of incubation, either naturally or artificially, during which time development of the young animal takes place. Many birds for example, sit on an egg or clutch of eggs in order to regulate temperature and humidity around the egg(s), such regulation being crucial for the survival and proper development of the embryo inside each egg. Other animals utilise different sources, for example solar or geothermal energy, for this purpose. Alternatively, incubation may be carried out and/or assisted by man. Man-made incubators are well known that can hold a number of eggs and which provide artificial temperature and humidity regulation of the air around the eggs.

Many breeders and conservationists of egg-laying animals need to know whether or not the embryo is alive and developing at the proper rate inside the egg. Such knowledge is required throughout the incubation period, and is important both in natural and artificial incubation scenarios in order to maximise the chances of survival of the young. In natural incubation, for example a clutch of eggs brooded by a bird, if one or more embryos does not survive, those eggs can become infected by bacteria and endanger the remaining eggs. Furthermore, some species of parrot for example the Palm Cockatoo, Black Cockatoo and Hyacinthine Macaw, can only lay fertile eggs during a short period of time each year and even then only incubate one egg at a time. If that egg does not survive, the opportunity for successful breeding has been missed for that year. Such scenarios can have serious implications for endangered species, and for breeders and keepers of such birds who exchange them for considerable sums of money. The situation is analogous for many species of egg-laying animal.

There are two well known methods for checking the fertility and development of eggs. The first method, known as "candling", involves placing an egg in front of an intense light source, for example tungsten halogen, so that the inside of the egg is visible to the naked eye, and looking for signs of growth e.g. vein development that is first visible after approximately four days in parrot eggs. Over the next few days it is possible to check for further growth by looking for increasing numbers and density of veins and a growing "dark spot" in the centre of the egg. However, there are three disadvantages with "candling", the first being that a high intensity of light is required to see into the egg meaning that it is exposed to high temperature levels that can damage or kill the embryo in the egg if held over the light for too long. Secondly, the "dark spot" grows at such a rate that after approximately twelve days (in parrot eggs) it occupies so much of the volume of the egg that the veins are no longer visible and it is not possible to tell whether or not the young bird is alive. Thirdly, some eggs are not suitable for "candling" such as raptors, falcons, ducks and wild fowl, whose eggs range from dark green to dark brown in cool, and other species whose shells are so dense that the light from the lamp cannot pass through them. For such eggs it is not possible to tell whether or not they are fertile and alive in the first few days.

The second known method addresses the second and third problems mentioned above. This method involves floating the egg in still warm water and waiting for the egg to move as a result of movement of the young animal inside. There are two disadvantages associated with this method, the first being that the method is unreliable and slow since it relies on a parameter that is inherently random. Secondly, immersing the egg in water exposes it to bacteria that can pass through the shell, particularly as the egg is withdrawn from the water, when water on the surface of the egg tends to be "sucked" in through the pores of the shell severely reducing the egg's ability to self-regulate humidity. Once inside the shell the bacteria and water are in an ideal environment at 37° C. to multiply, potentially endangering the life of the young animal.

Eggs undergo differing periods of incubation. For example, chicken eggs, as used in the commercial broiler industry, have an incubation period of 21 days. After approximately 50% of the incubation period, the animal in the egg has usually grown so much that conventional candling methods will offer little assistance in determining viability.

In a commercial environment a number of methods have been proposed for determining the viability of eggs, for example white broiler chickens, viz.:

U.S. Pat. No. 3,540,824 discloses a method of candling eggs using white light. Light in the wavelength range $6.5 \times 10^{-7}$ m to $8.5 \times 10^{-7}$ m is transmitted along the longitudinal axis of an egg with a light source positioned on its blunt end. A photoelectric sensor is positioned on the opposite end of the egg to detect light passing out of the egg over a wavelength range $7.3 \times 10^{-7}$ m to $7.5 \times 10^{-7}$ m with peak sensitivity at $7.35 \times 10^{-7}$ m. An output from the photoelectric sensor is filtered to reveal a heartbeat in the egg, if present.

There are a number problems associated with the apparatus described in U.S. Pat. No. 3,540,824 that make it unsuitable for reliable and efficient determination of the viability of eggs of at least 50% through their incubation period. Firstly, the white light source operates over a broad range of wavelengths. It will be noted that the photoelectric sensor is sensitive over a smaller range of wavelengths than are emitted into the egg by the light source, and that this smaller range borders the visible/infra-red boundary. The definition of the visible/infra-red boundary in terms of wavelength does not appear to be strictly defined in scientific dictionaries. For the purposes of the present invention it may be said to cover from more than $7.5 \times 10^{-7}$ m (750 nm) up to $1.0 \times 10^{-3}$ m (1 mm).

Light at visible wavelengths has a larger coefficient of absorption in tissue than light at infra-red wavelengths. The applicant has notices that the coefficient of absorption decreases as wavelength increases, such that infra-red having a wavelength in the visible/infra-red boundary will be more heavily attenuated in tissue than light with a wavelength in the middle of the infra-red part of the spectrum, for example. Accordingly, in order to obtain a signal with a detectable heart rate over the comparatively narrow range of wavelengths that the photoelectric sensor is sensitive, the light source must be relatively intense (one half or higher candle power is suggested in U.S. Pat. No. 3,540,824). As mentioned above, emitting intense visible light at the egg has an undesirable heating effect that can endanger the egg.

Secondly, as the embryo grows in the egg, more and more of the light from the light source will be absorbed for a given light intensity. The applicant has discovered that this problem is particularly acute in eggs of more than approximately 50% through their incubation period, for example 10 or 11 days in chicken eggs. Hence in the apparatus of U.S. Pat. No. 3,540,824, where both the light source and sensor lie on the longitudinal axis of the egg, a point will be reached where the sensor receives no useful signal. This problem is even more acute in chicken eggs of 16 to 18 days into incubation, just when viability needs to be determined for vaccination or gender sorting purposes for example. One way to deal with this might be to simply increase the intensity of the white light. However, this is highly undesirable for the reasons given above.

Thirdly, U.S. Pat. No. 3,540,824 mentions that movement of the chick affects the IR radiation received by the photoelectric sensor. It is stated that this does not affect operation of the apparatus in detecting a heartbeat. However, the applicant has found that this does not appear to be the case i.e. when the chick moves the applicant has found that it is not possible to detect the heart rate. Whilst is acknowledged by the applicant that the heartbeat will almost certainly be superimposed on the variation due to movement, the variation in the light intensity due to movement is so big that detection of heartbeat is very difficult while the chick moves.

JP-A-9 127 096 discloses an apparatus for determining the viability of a young egg, less than 10 days into its incubation period. Such eggs are much more transparent to light. The document does not say what type of light should be used, but it is clear that the light passes all the way into the egg, is scattered inside and is detected upon leaving the egg. Such methodology will not work reliably on eggs more than approximately 50% through their incubation period.

SU-A-1 597 173 discloses an apparatus for determining the viability of a young egg, less than 10 days into its incubation period. The document suggests that infra-red light be emitted through the pointed end of the egg, to be scattered inside the egg, and received back at the pointed end of the egg. Such methodology will not work reliably on eggs more than approximately 50% through their incubation period.

As acknowledged in U.S. Pat. No. 4,955,728 and U.S. Pat. No. 6,234,320 it is known to treat poultry embryos in ovo with, medication, nutrients and hormones, for example. This has the advantage that the appropriate treatment, for example vaccination, can be automated rather than given to the chick by hand shortly after hatch, thereby reducing costs. These methods are employed in the commercial poultry industry to decrease post-hatch mortality rates or increase growth rates of the hatched bird, for example. Typically, poultry eggs are injected on day 18 of their 21 day incubation period. Eggs are held in trays on racks in carts for incubation in relatively large incubators. At a selected time, typically on the $16^{th}$, $17^{th}$ or $18^{th}$ day of the incubation period, a cart of eggs is removed from the incubator for separating out non-viable eggs i.e. those that are dead or were not fertilised, from viable eggs. Those eggs that are determined to be viable are then sorted by gender or inoculated for example.

It is important to determine whether an embryo is alive or not in the egg before the relevant treatment is given. This is for a number or reasons including the financial cost of treating dead eggs and the fact that many dead eggs become infected with bacteria. If an injection system penetrates such a dead egg there is a high risk that the system will contaminate live eggs subsequently with this bacteria.

It is also desirable to sort birds by gender, particularly poultry, as described in WO-A-98/14781 for example. It is even more advantageous if this can be done before the bird hatches, i.e. in ovo, as considerable time and resources can be saved.

In performing vaccination and gender sorting as described above it is important that the available resources are used on viable eggs i.e. those that are alive. In many instances, an egg may not have been fertilised or may have died during incubation. It is important that these viable eggs are removed from the batch so that incubation, vaccination and gender sorting resources are not wasted on them. It is possible to remove the non-viable eggs. However, these have a tendency to "pop" when handled if they contain methane. The methane is generated by bacteria that infect the egg, putting the egg under gas pressure and making it especially fragile. If an egg bursts it may contaminate viable eggs, and so it is preferable to remove the viable eggs from the batch.

Heretofore, it has been difficult to reliably and quickly sort eggs that are alive from those that are dead, particularly in the commercial poultry farming industry.

Thus, it is apparent that there is a need for an apparatus and method of testing the viability of eggs from at least approximately 50% through their incubation period up to hatch that is more reliable, that minimises the risks to which prior methods have exposed eggs, and that does not require eggs to be positioned in a particular position during incubation and/or testing. Furthermore, there is a need for such an apparatus and method in which it is possible to distinguish between light intensity variation due to action of a heart and light intensity variation due to movement of the animal. There is also a particular need for a method and an apparatus that can determine the viability of a poultry egg when the egg is approximately 16 to 18 days into its incubation period of 21 days, prior to vaccination or gender sorting for example. There is yet a further need for a method and apparatus that provide an increased level of confidence in the result of a viability test on an egg or eggs.

SUMMARY OF THE INVENTION

The present invention is based on an insight into the effect that structures in viable eggs have on infra-red (IR) light passing therethrough or being reflected therefrom. This effect is present from approximately 5 to 12 days (depending on the species of animal) up until the animal hatches from the egg.

The invention is further based on the insight that it is possible to determine the viability of an egg by reflecting light at infra-red wavelengths from an outer (outward facing) surface of internal structures in the egg and receiving those reflected waves. When the egg, for example a poultry egg, is approximately 10-12 days old and older the embryo or chick can be of such an opacity that detection of action of a heart or movement of the chick on a light transmission basis is difficult without increasing the light intensity to unacceptable levels. By reflecting IR light from the outer (outward facing) surface of structures near the surface of the egg, viability can be determined without having to increase intensity of the IR light to overcome the opacity of the animal in the egg. Such structures may be vascular structures, in particular any blood carrying structure, for example the allanto-chorion, allantois, or other part of the animal in the egg that carries blood and that is near the surface of the egg.

The invention is yet further based on the insight that the reliability of heart rate detection can be improved by selection of an emitter and detector that have a sufficiently narrow spectrum in the infra-red wavelength band respectively.

A further insight upon which the present invention is based is that shielding means to shield an egg from background infra-red radiation during testing can be dispensed with in some circumstances. This is where sufficient power is available to power a narrowband (in terms of wavelength) detector in the infra-red part of the spectrum. This reduces the need to deal with a background light artefact (not necessarily in the infra-red part of the spectrum) in the signal from the detector. In some embodiments, particularly where the apparatus is battery powered, it is necessary to use a broadband detector for power/sensitivity considerations and to filter the background light artefact out of the received signal by electronic processing.

The present invention is further based on the insight that the viability of an egg can be determined by examining a signal representative of infra-red light that has passed through and/or been reflected from the internal structures of the egg for two criteria. These are (i) a cyclical variation in the signal representative of a heartbeat, and (ii) a variation representative of movement of the animal in the egg. The applicant has devised a way to differentiate between (i) and (ii) with appropriate algorithms, the existence of either indicating that the egg is viable. In one embodiment this can be done by examining the frequency and amplitude of the signal generated by the light at the detector. A heart beat will generate variations in light intensity within an expected frequency range and amplitude. Movement of the animal will generate signal variation with a much larger amplitude than that caused by action of a heart. This enables the confidence in the result to be increased, and the speed and accuracy of testing to be improved.

It should be noted that embodiments of the invention do not rely upon all of the above insights in combination. Rather, embodiments may rely upon one or more of these insights, or any combination thereof.

According to one aspect of the present invention, there is provided a method of determining the viability of an egg at least approximately 50% through its incubation period, which method comprises the steps of:

(a) causing electromagnetic radiation to impinge upon the egg, the electromagnetic radiation having one or more wavelengths in the infra-red part of the spectrum;

(b) receiving at least a part of the infra-red radiation that has passed through the egg and generating an output signal representative of the received infra-red radiation; and (c) processing said output signal to determine whether there is a cyclical variation in the intensity of the infra-red radiation leaving the egg corresponding to action of a heart, the existence of said cyclical variation indicating that the egg is viable;

wherein step (a) is performed by directing infra-red radiation so that it passes through the shell for reflection from an outer surface of a vascular structure adjacent an inner surface of said shell, and step (b) is performed by receiving any infra-red radiation so reflected. The outer surface may be an outward facing surface. By reflecting light from internal vascular structures in the egg, for example structures adjacent the air-sac, it is possible to determine the viability of the egg in the late stages of incubation when the animal is relatively opaque, for example 16, 17 or 18 days in poultry eggs. The method will also work on young eggs (i.e. less than 50% through their incubation period), thereby enabling more reliable testing throughout the incubation period. The light can be emitted so that it passes through the air-sac, impinges on and is reflected from the allantois (or allanto-chorion) adjacent the air-sac. In this way IR light does not have to pass through the body of the animal, which in the late stages of incubation can be relatively opaque to IR light such that no useful signal can be obtained without increasing the intensity of the light to unacceptably high levels. The method may further comprise the step of shielding the egg from background light during testing. This may be important when testing batches of eggs in sequence such that the receiving means would otherwise be exposed to background light in between testing. The receiving means is likely to output a signal representative of saturation between testing of eggs if the method is performed in the presence of background lighting e.g. daylight or artificial lighting. There will be a short settling time of the receiving means and circuitry when the next egg moves adjacent the receiving means before testing can commence. This time can be reduced by appropriate use of shielding. In other embodiments shielding may be desirable to improve reliability of testing, and in particular to inhibit the processing means seeing variation in intensity of background light as movement of the animal within the egg. Alternatively, the method may be performed substantially in the dark.

One particular advantage of at least preferred embodiments of the present invention is that an initial indication of viability can be made quickly (e.g. within one or two seconds) such that the egg can be tested substantially continuously or repeatedly over a period of between approximately 5 and 10 seconds for example to increase confidence in the final result. During this time an indication of viability, such as cyclical variation or a signal indicating movement of the animal, can be repeatedly looked for. Each time such an indication is found during the time period it may be electronically recorded. At the end of the time period, it is possible to electronically examine the record to determine viability with increased confidence. In this way the chances of a spurious noise signal leading to a positive result is reduced, because the egg is repeatedly tested over a given time period.

It is possible to operate the method at any position around the egg. Since the vascular structures may be adjacent substantially all of the inner surface of the egg and air-sac, reflected light is likely to have a cyclical variation if the egg is viable. The applicant has found that reflecting light from the vascular structures (e.g. allanto-chorion) adjacent the air-sac gives particularly good results. It is believed that this is due to the substantially flat surface formed by the air-sac and therefore by the allanto-chorion that is pressed against it, and due to its surface area. These two factors increase the proportion of IR light reflected towards the detector. If using the method on another part of the egg where the allantois presents a more convex surface to incoming IR light, it would be possible to improve results by collecting reflected light with a reflecting means, for example a parabolic mirror, and focusing the light onto the receiving means.

In one embodiment the emitting means and the receiving means have a emitting axis and a receiving axis respectively, the arrangement being such that, in use, the angle between the emitting axis and receiving axis is less than 90°, with between 30° and 60° being preferable and approximately 45° yet more preferable. These angles produce particularly good results when the detector is positioned substantially on the longitudinal axis of the egg and one or more emitters (or vice versa) is positioned relative thereto. When the method is performed in a glancing mode, the angle between the emitter axis and detector axis may 180° or less. Preferably, the emitter and detector axis in this method are not co-axial with the longitudinal axis of the egg, although they may be co-axial with one another. One or other may be co-axial with the longitudinal axis of the egg.

In another embodiment, the method further comprises the step of moving the receiving means with respect to the egg during testing to seek the strongest reflected component of the IR radiation. This movement may be around the longitudinal axis of the egg and/or along the longitudinal axis.

According to another aspect of the present invention, the above method is performed by glancing infra-red radiation from the egg instead of or in addition to reflecting it. When the egg is opaque, a useful signal can be obtained by directing IR radiation toward the air-sac near the edge of the shell and receiving radiation that has passed through this small portion of the egg.

Further steps of the method are set out in claims 2 to 30 to which attention is hereby directed.

Preferably, the method further comprises the step of extracting the time interval between successive points in the cyclical variation in order to calculate a heart rate therefrom. The method may further comprise the steps of comparing the calculated heart rate against a predetermined range to ensure that the calculated heart rate lies within the range to inhibit the effect of random noise.

Advantageously, the method further comprises the step of extracting a plurality of time intervals, and calculating an average time interval and heart rate therefrom.

According to another aspect of the present invention, there is provided an apparatus for determining the viability of an egg at least approximately 50% through its incubation period, which apparatus comprises emitting means for causing electromagnetic radiation to impinge upon an egg, the electromagnetic radiation having one or more wavelengths in the infra-red part of the spectrum, receiving means for receiving at least a part of the infra-red radiation that has passed through the egg and generating an output signal representative of the received infra-red radiation, and processing means for processing said output signal to determine whether there is a cyclical variation in the intensity of the infra-red radiation leaving the egg corresponding to action of a heart, the existence of said cyclical variation indicating that the egg is viable, the arrangement being such that, in use, said emitting means are positioned to direct infra-red radiation so that it passes through the shell for reflection from an outer surface of a vascular structure adjacent an inner surface of said shell and said receiving means are positioned to receive any infra-red radiation so reflected.

Further features of the apparatus are set out in claims 34 to 64 to which attention is hereby directed.

The use of infra-red light in the method and apparatus is preferred for two reasons, (1) attenuation of infra-red light passing through eggs is much lower than with light at optical wavelengths, and (2) infra-red light can impinge on the egg for a much longer period without heating the egg. The egg can be damaged by heat when candling with optical light if the egg is left in front of the optical source for too long. For the purposes of the present invention the infra-red part of the spectrum may be taken to be that between more than $7.5 \times 10^{-7}$ m and about $1.0 \times 10^{-3}$ m. In one embodiment the emitting means emits light in the infra-red part of the spectrum over a wavelength range of approximately $8.0 \times 10^{-7}$ m to $1.5 \times 10^{-6}$ m with peak intensity at $9.4 \times 10^{-7}$ m; and the receiving means receives IR radiation over a wavelength range of approximately $8.0 \times 10^{-7}$ to $1.1 \times 10^{-6}$ m with peak sensitivity at $9.4 \times 10^{-7}$ m. It is advantageous if the detecting means has a peak sensitivity at a wavelength of approximately $9.4 \times 10^{-7}$ m or longer as the applicant has found that performance increases with the wavelength of infra-red used. If the detected wavelength is too near the visible part of the spectrum, attenuation of light increases and accuracy of the method and apparatus falls.

Although the applicant expects that the periodic attenuation of the received radiation might be superimposed on optical light, it is too dangerous to place the egg in front of an optical light source to enable the apparatus of the invention to obtain the cyclical variation as proposed by U.S. Pat. No. 3,540,824. This is because in order to penetrate and pass right through the egg, particularly in dark pigment eggs and those late in the stages of incubation, light at optical wavelengths must be of such intensity that the egg is in danger of becoming overheated if left near the light source for any appreciable length of time (more than 3 or 4 seconds).

One advantage of at least preferred arrangements is that a signal representing the viability of a plurality of eggs can be generated and used in a sorting apparatus to remove the non-viable eggs before the remaining eggs are sorted by gender and/or inoculated. In this way resources are only expended on viable eggs.

Advantageously, the apparatus further comprises means for providing a visual display trace on which any cyclical variation is apparent. This may be for an egg whose viability cannot be determined automatically by the method and apparatus of the invention. In one embodiment where a plurality of eggs being tested simultaneously the apparatus may comprise means for removing each egg whose viability cannot be determined, and means for generating a signal to alert an operator to inspect the egg manually.

According to another aspect of the present invention there is provided an apparatus for determining the viability of a plurality of eggs, which apparatus comprises a plurality of apparatus as set out above, means for holding a plurality of eggs adjacent said plurality of apparatus, means for moving said plurality of apparatus into and out of engagement with the plurality of eggs and means for generating an output signal indicative of those eggs that are viable and/or those eggs that are not viable.

According to another aspect of the present invention there is provided, for use in an apparatus as aforesaid, a common body having the common body features as set out in the appended claims, a plurality of infra-red emitting means, an infra-red detecting means and means for mounting the common body on an viability testing apparatus. A common body having these features may be manufactured and sold as a spare part for use with an apparatus in accordance with the invention.

According to another aspect of the present invention there is provided a method of producing chickens, which method comprises the steps of:

(1) incubating a plurality of eggs;

(2) testing the viability of each egg of the plurality of eggs anywhere between approximately 16 and 18 days into their 21 day incubation period;

(3) inoculating those eggs determined to be viable; and (4) further incubating the inoculated eggs to hatch;

wherein the viability test is carried out by the method as set out in the appended claims.

According to another aspect of the present invention there is provided a method of propagating a vaccine, which method comprises the steps of:

(1) placing a live virus in plurality of eggs;

(2) incubating the plurality eggs;

(3) testing the viability of each egg of the plurality of eggs; and (4) harvesting virus-rich parts of those eggs determined to be viable;

wherein the viability test is carried out by the method as set out in the appended claims.

Preferably, said processing means can determine a heart rate and said apparatus further comprises means for a displaying a numerical indication of the heart rate.

Advantageously, the processing means extracts only variation in the output signal.

Preferably, the apparatus further comprises means for applying a gain to said output signal or cyclical variation. The gain may be between approximately 1500 and 20000.

Advantageously, said processing means can filter the output signal to remove at least some of the noise in the output signal.

Preferably, said processing means can extract the time interval between successive points in the cyclical variation in order to calculate a heart rate therefrom.

Advantageously, said processing means can compare the calculated heart rate against a predetermined range to ensure that the calculated heart rate lies within the range to inhibit the effect of random noise.

Preferably, said processing means can extract a plurality of time intervals, and is able to calculate an average time interval and an average heart rate therefrom. The processing means can compare the calculated average heart rate against a predetermined range to ensure that the calculated average heart rate lies within the range to inhibit the effect of random noise.

Advantageously, said processing means perform step (c) by determining whether the magnitude of said output signal lies above a first predetermined threshold based upon an expected magnitude due to action of a heart.

Preferably, said processing means can process said output signal to determine whether there is a variation in the intensity of the infra-red radiation leaving the egg corresponding to movement of an animal within the egg.

Advantageously, determination of movement of the animal within the egg by said processing means is performed by determining whether the magnitude of said output signal lies above a second predetermined threshold based upon the expected magnitude of the signal due to movement of the animal.

Preferably, said apparatus can generate a signal indicating that the egg is viable in response to detection in said output signal of either said cyclical variation due to action of a heart or said variation due to movement of the animal within the egg.

Advantageously, the receiving means are shielded from detecting electromagnetic radiation emitted directly from said emitting means. This helps to ensure that the output from the receiving means is meaningful. Since some radiation is reflected off the shell of the egg, this shielding also inhibits radiation that has not passed through the egg from reaching the receiving means.

Preferably, the receiving means is positioned to inhibit detection of electromagnetic radiation emitted directly from said emitting means. In one embodiment, the receiving means is shielded by positioning so that, in use, the egg lies between the emitting means and receiving means. In another embodiment, the receiving means is both positioned to inhibit detection of electromagnetic radiation emitted directly from said emitting means and provided with a physical shield.

Advantageously, said emitting means emit electromagnetic radiation over a limited angle. This helps to ensure that the receiving means only detects radiation that has passed through the egg.

Preferably, the limited angle is adjustable. By making the angle adjustable, and hence the amount of infra-red impinging on the egg, a user is able to adjust the apparatus to achieve an optimum output from the receiving means. In one embodiment the apparatus is provided with a plurality of emitting means that each have a different limited angle. In use, a user can switch between each emitting means to obtain the best results.

Advantageously, the apparatus further comprises a support means for supporting an egg in a position within the apparatus. The support means may be tray for holding a plurality of eggs, moveable into and out of a position adjacent the eggs to be tested.

Preferably, the receiving means is located adjacent said support means. In one embodiment the receiving means is located within said support means, the arrangement being such that, in use, electromagnetic radiation can reach the receiving means only by passing through the egg. This is particularly advantageous because, in use, the egg and support means enclose the receiving means so that only radiation that has passed through the egg can be detected.

Advantageously, the support means comprises a deformable material that provides a point of contact with an egg, the material deforming to part of the contours of the egg under the egg's weight. This provides a "seal" inhibiting penetration of unwanted infra-red radiation, that might be detected by the receiving means.

Preferably, the deformable material comprises latex. In one embodiment, the latex comprises a black dye. The applicant has found this particularly effective since the combination inhibits penetration of unwanted infra-red radiation and at the same time provides a support that minimises potential for damage to the egg.

Advantageously, the support means comprises a suction cup. In one embodiment the receiving means are mounted in the suction cup.

Preferably, said shielding means comprises a housing having a first member and a second member moveable with respect to the first member from a position in which an egg can be inserted into the apparatus to a position in which the egg is shielded from background infra-red radiation. In one embodiment, the receiving means and emitting means are mounted on the first member.

BRIEF DESCRIPTION OF THE DRAWINGS

For a better understanding of the present invention, reference will now be made by way of example to the accompanying drawings in which.

DETAILED DESCRIPTION OF THE PREFERRED EMBODIMENTS

Figure 1:
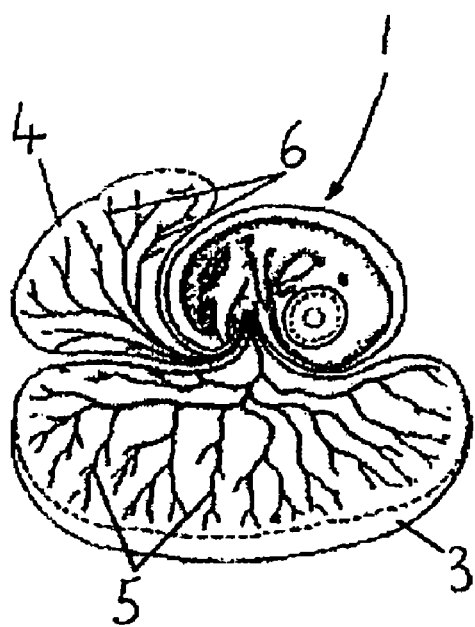
FIG. 1 is a schematic cross section through a seven-day old chicken embryo showing its embryonic membranes and embryonic blood vessels.
Figure 2:
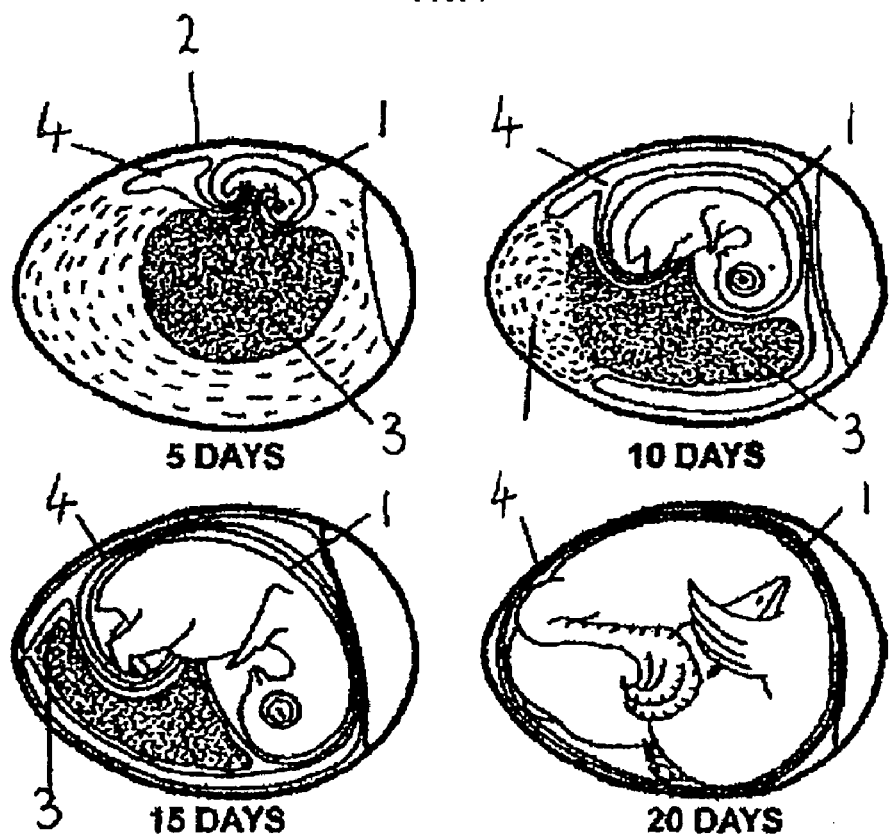
FIG. 2 is a schematic cross section through an egg containing the embryo of FIG. 1 shown at four points during its development.

Referring to FIGS. 1 and 2, for an understanding of the background to the present invention some details of a poultry or chicken embryo 1 developing within a shell 2 are shown. It is to be noted that the structure of the chicken egg is very similar to that of a wide variety of egg-laying animals. The embryo 1 comprises a yolk sac 3 within which blood vessels 5, known as the vitelline vessels, extract nutrients and convey them to the embryo. Another structure 4 known as the allantois assists the respiratory cycle of the embryo. As the embryo 1 grows the allantois 4 (or allantochorion) is pressed against the inner surface of the shell 2 where the capillaries in the allantois can readily exchange carbon dioxide for oxygen that has passed through the pores of the shell. Under action of the animal's heart the blood vessels 6 in the allantois 4 swell and contract in a cyclical fashion. Furthermore, as is apparent from FIG. 2, the allantois 4 grows as the embryo 1 develops so that it covers an increasing surface area adjacent the inner side of the shell 2. The respiratory function of the allantois 4 begins approximately at three to four days from the beginning of the incubation period and ceases when the chick breaks out of the egg and breathes of its own accord.

Figure 3:
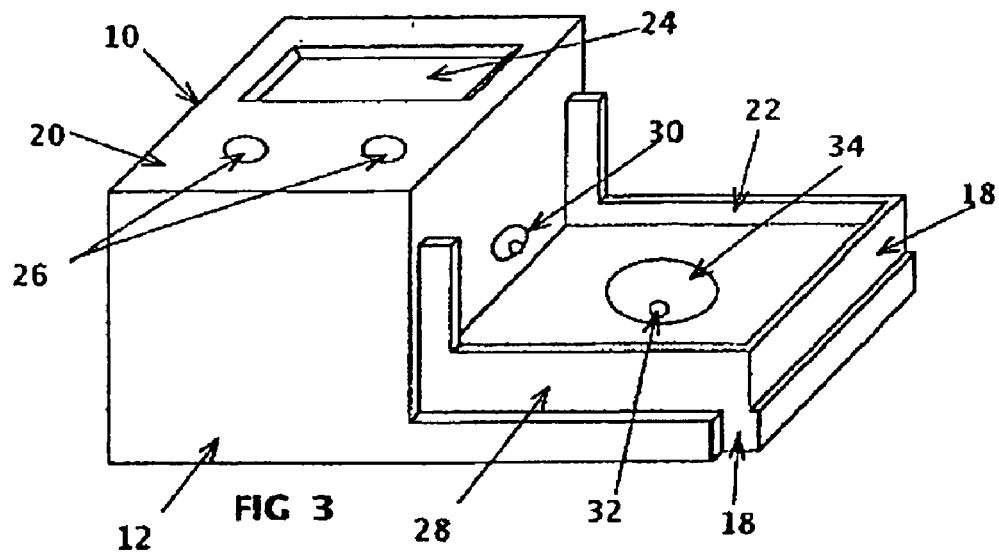
FIG. 3 is a schematic perspective view of part of a first embodiment of an apparatus in accordance with the present invention, the lid being removed for clarity.

Referring to FIGS. 3 to 6, an apparatus generally identified by reference numeral 10 comprises a housing 12 and a lid 14. As shown in FIG. 3, the lid 14 can be mounted on the housing 12 via inward projections 16 on the lid 14 that locate with recesses 18 on the housing 12 and permit rotational movement of the lid 14 with respect to the housing 12. The lid 14 is constructed from plastics material that prevents the passage of infra-red radiation through its walls.

The housing 12 comprises two sections, a first section 20 and a second section 22. The first section 20 comprises a liquid crystal display 24, control buttons 26, a power source (not shown) and various electronic processing equipment (not shown) that will be described in greater detail below. The second section 22 comprises a box 28 open at its upper side and having five walls constructed from plastics material that prevent passage of infra-red radiation. Thus, when the lid 14 is in a closed position on the box 28 the volume that is enclosed is shielded from background infra-red radiation. A source 30 is mounted on the box 28 adjacent the second section 22 and is positioned so that it can emit electromagnetic radiation into the box 28. The source 30 is an infra-red (IR) emitter manufactured and sold by Kodenshi Corporation (part number OPE5594A) that can emit IR over a wavelength range of $8.95 \times 10^{-7}$ m-$1.4 \times 10^{-6}$ m, with peak intensity at approximately $9.4 \times 10^{-7}$ m and a beam angle of 20°. The axis of the beam lies on a perpendicular to plane of the wall on which it is mounted. The applicant has found that the power of infra-red from the source 30 does not appear to cause any damage to the egg under test. An infra-red detector 32 is mounted in the base of box 28 and is designed and positioned to detect IR that has been emitted by the source 30. The detector 32 is manufactured by Texas Instruments as component TSL 250R and is available from Pacer Components (Berkshire, England). The detector 32 can detect light over a wavelength range of $3.0 \times 10^{-7}$ m to $1.1 \times 10^{-6}$ m with a peak response at approximately $7.8 \times 10^{-7}$ m. It will be noted that the radiation emitted from the source 30 does not directly intersect with the detector 32.

Figure 4:
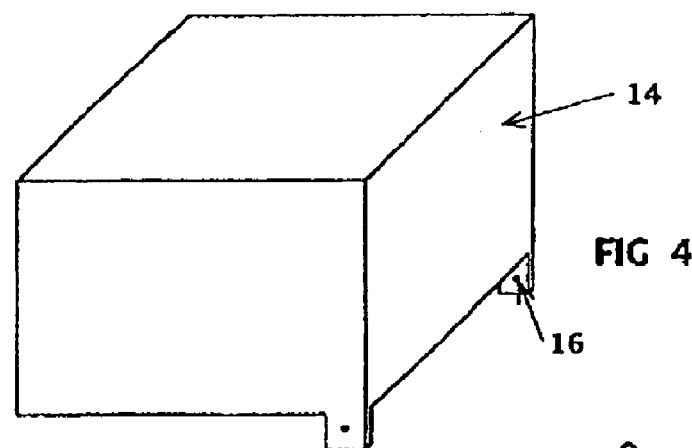
FIG. 4 is a schematic perspective view of a lid suitable for use with the apparatus of FIG. 3.

Mounted on the bottom of the box 28 and around the detector 32 is a holder 34 that comprises an inverted suction cup manufactured from latex so as to be deformable. The suction cup is different to known suction cups in that a black dye has been added during manufacture to inhibit passage of light at infra-red wavelengths. In use, an egg can be placed on and supported by the holder 34 and the latex deforms to the contours of that part of the egg with which it is in contact. The egg can be supported in any orientation by the holder 34. No suction is applied via the holder 34. The distance x as shown in FIG. 4 is 0.05 m, although this does not appear critical and the source 30 may abut an egg or be further away.

Figure 5:
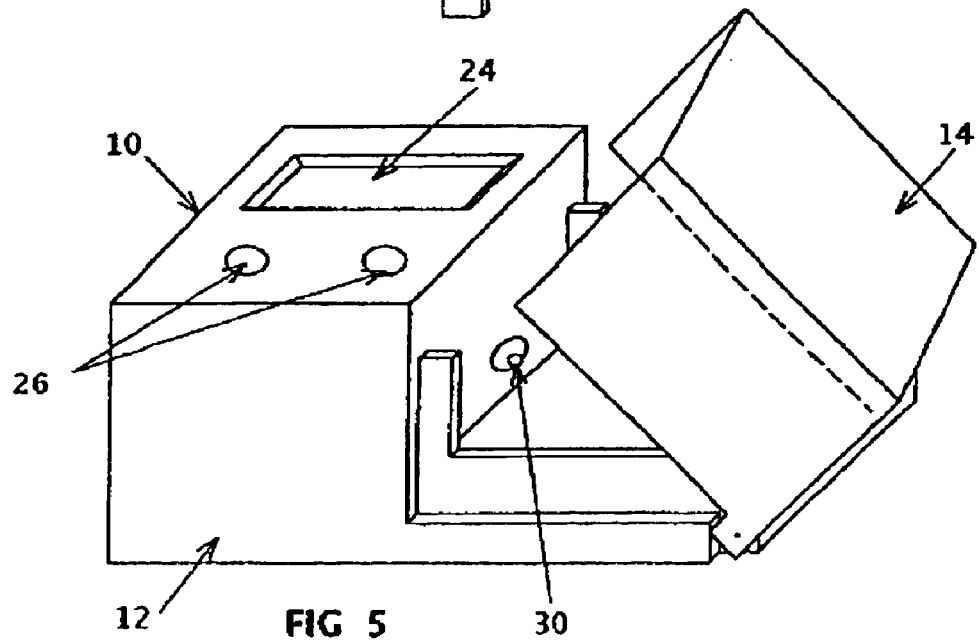
FIG. 5 is a schematic view of the apparatus of FIG. 1 fitted with the lid of FIG. 4.

In use, the lid 14 of the apparatus 10 is opened and an egg 36 (see FIG. 6) who's viability is to be determined is placed on the holder 34. The lid 14 is closed, placing the egg 34 in darkness and shielding it from IR. One of the buttons 26 on the housing 12 is pressed and, under control of electronic circuitry (not shown) in the second section 22, source 30 is activated and emits IR radiation 38 toward the egg 34 continuously until the apparatus is de-activated by the user. Upon reaching the egg 34 part of the radiation 38 is reflected off the shell of the egg 34 and part passes through the shell into the inside of the egg. It will be noted that the holder 34 inhibits radiation that has been reflected from the outside of the egg from being detected by the detector 32. As shown in FIG. 5 some of radiation 38 is repeatedly reflected off the inner side of the shell, some passes straight through and some is ultimately reflected through 90° i.e. in the direction of detector 32. Upon leaving the egg 34 it is likely that some radiation 38 passes across the allantois (not shown in FIG. 6) inside the shell, and when in the early stages of incubation across the yolk sac containing the vitelline vessels. As described above, the allantois is responsible for intake of oxygen and expulsion of $CO_2$ from the egg as part of the respiratory cycle of the developing animal. Blood vessels inside this membrane continually swell and contract under the action of the animal's heart. Accordingly, as IR radiation 38 passes across this structure, some has to pass through more blood (when the blood vessels are swollen or swelling) and some passes through less blood (when the blood vessels are contracted or contracting). This results in a cyclical variation in the intensity of the IR radiation leaving the egg 36 that is a direct function of the animal's heart rate. The electrical output signal from the detector 32 also varies in the same way, the variation being of the order of approximately 0.2 mV to 1 mV. It is believed that is it is the blood vessels in the allanto-chorion that are primarily responsible for causing the cyclical variation in intensity of received infrared. However, it might be possible that other structures are responsible for the cyclical variation, particularly the vitelline vessels when the egg is in the early stages of incubation and the yolk sac is still large.

Figure 7:
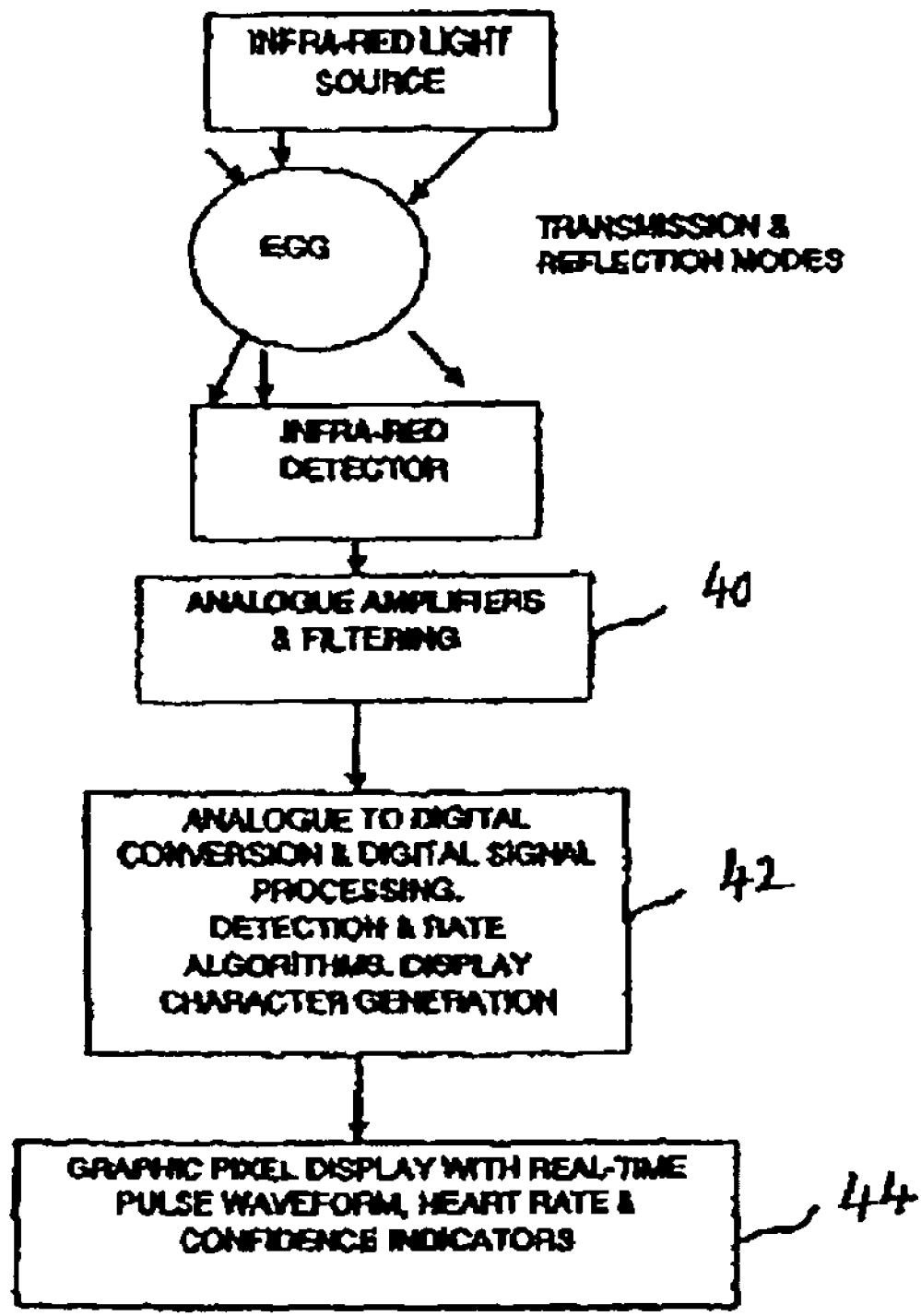
FIG. 7 is a flow diagram showing the steps of a method in accordance with the present invention.

Referring to FIG. 7 the output signal from the detector 32 is processed by electronic processing equipment located in the first section 20 of the housing 12. The signal is first amplified and then filtered at stage 40.

Figure 8:
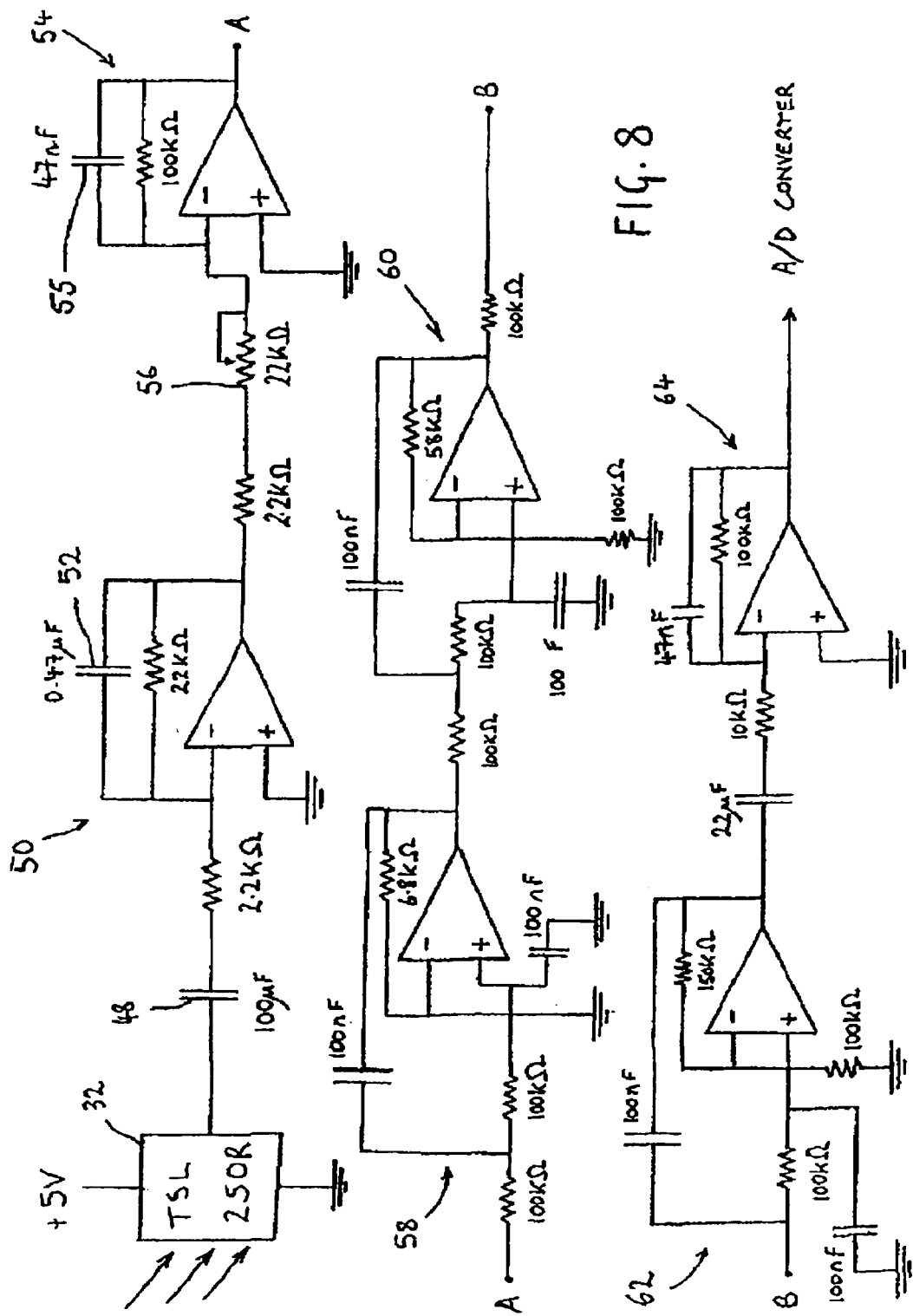
FIG. 8 is a circuit diagram of the amplification and filtering stages of the apparatus of FIG. 3.

Stage 40 is shown in greater detail in FIG. 8. The output signal from the detector is of the order of approximately 200 mV upon which the time varying voltage of the order of a few mV is superimposed as described above. It is this time varying signal that the circuitry is designed to extract and amplify. The output signal first passes through a capacitor 48 to extract the time varying part of the signal. This time varying signal passes to a first gain stage 50 that applies a gain of 10 and also filters the signal with the capacitor 52. The capacitor 52 acts as a low pass filter with a filter corner frequency of 15 Hz i.e. the 15 Hz component of the input signal is reduced by 3 dB at this stage. 15 Hz corresponds to a heart rate of approximately 900 beats per minute, over which it is unlikely any animal's heart will beat, but also well below the 50 Hz signal generated by mains electricity. The signal then passes to a second gain stage 54 that applies a gain of between 4.13 and 45.45, depending on the value of variable resistor 56 (variable between 0 and 22 kΩ). The signal is also filtered at stage 54, the capacitor 55 being a low pass filter with a filter corner frequency of 33 Hz i.e. the 33 Hz component of the input signal is reduced by 3 dB at this stage. Because of electrical interference in the wires generated for example by induction from mains power lines it is necessary to further filter the signal; if the signal is not further filtered the time varying signal corresponding to the variation in intensity of the received IR would be totally drowned out by interference and noise. Accordingly, the signal then passes through a first filter stage 58 that applies a gain of 1.068,onto a second filter stage 60 that applies a gain of 1.58 and onto a third filter stage 62 that applies a gain of 2.50. Each filter stage is a low pass filter having a filter corner frequency set at 16 Hz i.e. the 16 Hz component of the input signal is reduced by 3 dB at each stage. Having been filtered, the signal passes through a final third gain stage 64 that applies a gain of 10 and a final low pass filtering of the signal with a corner frequency at 33 Hz. Accordingly the overall gain on the time varying signal is between 1742 and 19180 remembering that this is because of the variable resistor 56, and the signal has been filtered at 24 dB per octave (mainly due to the effect of filtering at stages 50, 58, 60 and 62). In the actual apparatus made by the applicant the variable resistor 56 can be adjusted at the point of manufacture and is set to give the maximum gain. However, it is not adjustable by the user. The signal then leaves this section of the apparatus and moves onto the analogue to digital converter.

Referring again to FIG. 7 at stage 42 the signal is converted from analogue to digital and processed by a microcontroller (not shown). The steps of the digital signal processing are shown in greater detail in FIG. 9. The microcontroller is programmed to set up a band stop filter 84, that is it looks for that part of the signal having voltage amplitude greater than a preset voltage and that part of the signal having voltage amplitude lower than a preset voltage. The values of the band stop filter are between 2.0V and 2.9V. The time varying signal with which the apparatus is concerned is periodic by nature and when an egg is appropriately positioned the peaks 86, 88 of this signal will appear at either side of the band stop filter. Random error noise 90 will also occasionally appear at either side of the band stop filter; however, the algorithms programmed into the microcontroller are designed to extract the periodic signal and reject signals generated by random error noise that may not be hidden by the band stop filter.

Figure 9:
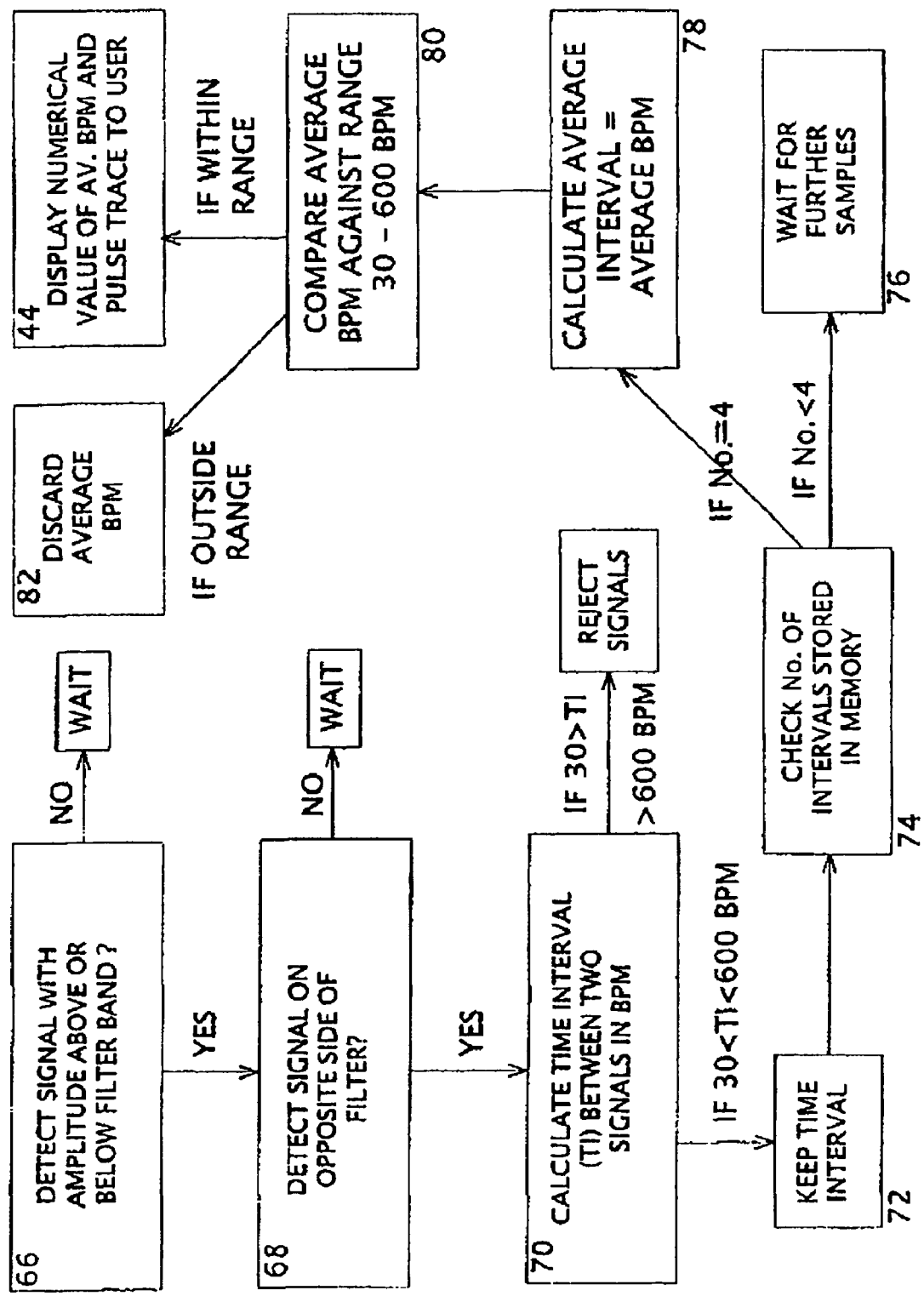
FIG. 9 is a block diagram of the algorithm used to manipulate the amplified output signal of the detector used in the apparatus of FIG. 3.
Figure 10:
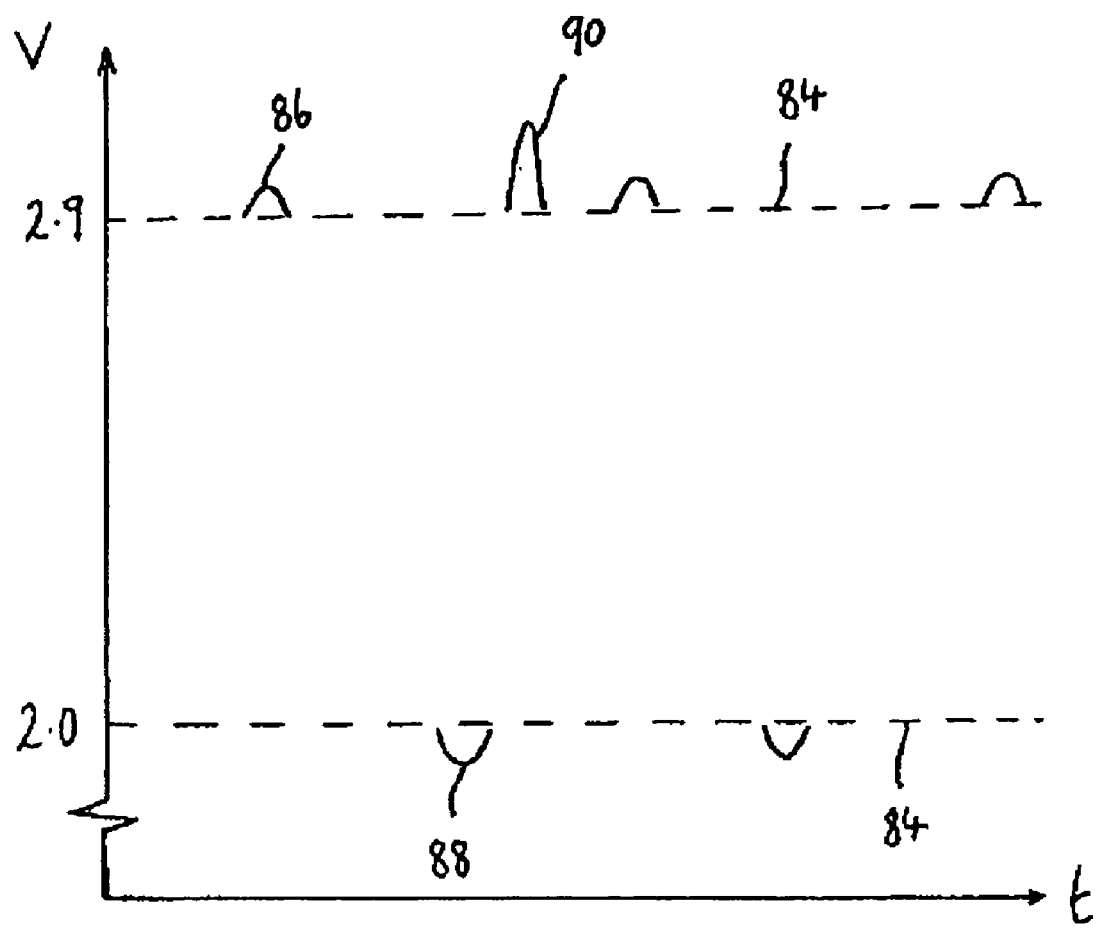
FIG. 10 is a schematic graph showing the method of detecting the cyclical variation in intensity of light received by the detector.

Referring to FIGS. 9 and 10 the first step 66 of the algorithm involves monitoring the band stop filter 84 and waiting for a signal to appear at either side. This monitoring is continuous. Whilst the algorithm is waiting for its first pair of signals 86, 88 the user sees a flat trace on the display and the numerical value of beats per minute displayed to the user is zero. When a first signal 86 does appear, the algorithm moves to step 68 in which it looks for a second signal 88; if it does not detect one it simply continues to wait whilst still monitoring. If the algorithm does detect a second signal 88 it moves to step 70 in which the time interval in beats per minute (bpm) is calculated between the detection of the first signal 86 and detection of the second signal 88. In the same stage the algorithm checks whether the calculated time interval falls within the range 30 to 600 bpm; if it does not the signals are rejected, whereas if it does the algorithm moves to step 72 in which the time interval is stored in the microcontroller's memory. At step 74 the algorithm checks the number of intervals that are stored in memory. If the number is less than four, it waits for further time intervals to be received at step 76. If the number is equal to four the algorithm calculates the average bpm from the four intervals at step 78. Using four intervals to calculate the average bpm is useful as this reduces the chance of noise affecting the result. A further advantage is that the average bpm will vary more gradually than a real time display of the bpm that may fluctuate rapidly. Finally, the algorithm checks that the calculated average bpm lies in the range 30 to 600 bpm at stage 80 (an animal's heart rate is unlikely to go above 600 bpm; at present a high heart rate that the applicant has measured was 250 bpm in a chicken egg (bantam)). If it is not, the calculated average is discarded at stage 82. If it is in the range the numerical value of bpm is displayed to the user on display 24 at stage 44 (see FIG. 7) together with a trace of voltage versus time that represents the heart rate of the animal in the egg. The trace is generated from the actual output signal, although it could be generated from the calculated average bpm. However, using the output signal enables the user to see if the apparatus has generated a spurious result, for example if there is a lot of repetitive noise in the signal. It should be noted that the microcontroller only ever stores a maximum of four intervals. When a new interval is received the oldest interval is removed to make room for the new interval. In this manner the information displayed to the user is always the latest and effectively provides a real time display of the heart rate of the animal.

Figure 11:
FIGS. 11, 12 and 13 show various examples of traces of voltage (Y-axis) against time (X-axis) that can been seen on a screen of an apparatus in accordance with the present invention.
Figure 12:

If no cyclical variation is obtained from the detector the display 24 indicates that the egg is not viable and the trace shows a flat line indicating IR being received by the detector 32 at a constant rate (FIG. 11). If the egg is viable a trace similar to that shown in FIG. 12 is seen.

Figure 13:

The applicant has found that, even if the egg is viable, it is not always possible to obtain a satisfactory output from the detector 32. In particular, this occurs if the animal moves inside the egg or if the infra-red does not pass through a sufficiently big blood vessel as it exits the egg. If the animal is moving the trace on display 24 is rapid, erratic and the pulse is exaggerated. If the egg is in a bad position, the trace shows faint pulse line i.e. greatly reduced in magnitude (FIG. 13), but not a flat line as with a non-viable egg. In this situation, the algorithms at stage 42 cause the display to show a signal to the user either that animal is moving or that the egg is badly positioned which prompts the user to wait or re-position the egg. A user may need to re-position the egg between 1 and 3 times to be sure that an egg is not viable, and preferably repeat the process at several intervals of 24 hours in order to be completely sure that the egg is not viable. Although the apparatus indicates the viability almost immediately, the eggs of some species are too valuable to discard on the basis of one reading. The electronic processing equipment continually monitors the received signal and as soon as a viable signal is received the heart rate trace and beats per minute are displayed.

The applicant has also found that a good signal is obtained when the radiation impinges on an egg from its side i.e. substantially perpendicular to its longitudinal axis, and the detector 32 is located below the egg with its detection axis substantially perpendicular to the axis of the source 30. However, in the early stages of development of the egg, the detector 30 and source 32 can be placed anywhere around the egg or the egg placed at any orientation within the apparatus 10 to obtain a signal. When the egg is more developed, the animal occupies so much of the volume of the egg that only a narrow range of positions obtains a satisfactory signal. One of these positions is shown in FIG. 4 and is further advantageous because the egg can be readily supported in this position. The applicant has also found that when nearly fully developed, the best signals are obtained when the radiation impinges on the rounded or "blunt" end of the egg, passes through the air sack inside and is reflected from vascular structures inside the egg, thus still passing through the structures mentioned above but not being obstructed by the animal.

Important variations of the above embodiment are that the electronic processing equipment may be separate from the box in which the egg is placed i.e. the first section 20 may be separate from the second section 22. If no signal is obtained from the receiving means, the display 24 may prompt the user to move the egg and/or re-activate the apparatus so that the viability is determined over a number of interrogations, thus minimising the chances of error.

The apparatus may be incorporated into known incubators to provide an "all-in-one" arrangement for incubating eggs.

The apparatus described in the preferred embodiment is designed to be hand-held and portable. However, this is not essential.

The apparatus above may be powered by mains electricity in which case the lid can be omitted as more power is available to power a narrowband IR detector. This reduces the need to block out background light. Alternatively, the particular emitter and detector described below can be used in the embodiment above.

Figure 14:
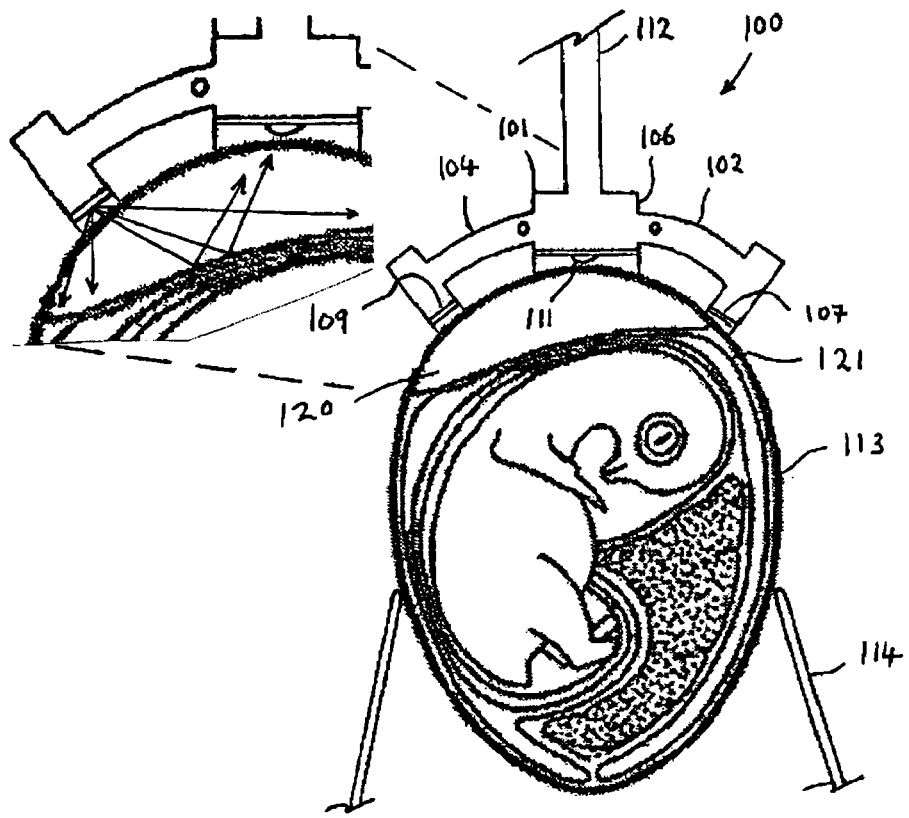
FIG. 14 is a schematic view of a second embodiment of an apparatus in accordance with the present invention with an egg positioned in a testing position therein, together with a close-up view of part of the apparatus testing the egg.
Figure 15:
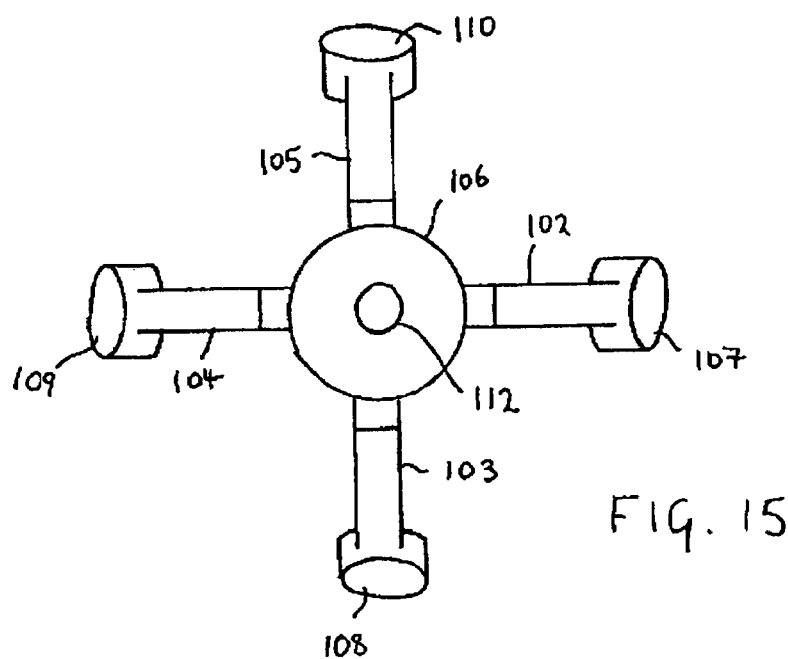
FIG. 15 is a plan view of the apparatus of FIG. 14.

Referring to FIGS. 14 and 15 a second embodiment of an apparatus generally identified by reference numeral 100 comprises a mount 101 having four arms 102, 103, 104 and 105, equi-circumferentially spaced around a central portion 106. Each arm 102, 103, 104 and 105 is of arcuate shape, constructed from plastics material and pivotally mounted on the central portion 106. Each arm 102, 103, 104 and 105 can pivot independently about a respective projection on the central portion 106. Each arm is also biased downwardly (in the sense of FIG. 14) by a respective spring (not shown) whose function will be described in greater detail below. At the end of each arm 102, 103, 104 and 105 is a surface mount infra-red light source 107, 108, 109 and 110. Each infra-red light source is part number SMT940 manufactured by Epitex, Inc., available from Pacer Components, Berkshire England, that can emit IR with peak intensity at $9.4 \times 10^{-7}$ m (940 nm) and has a half-width of 50 nm. Mounted in the central portion 106 is a proximity sensor (not shown) and an infra-red detector 111 that is manufactured by Texas Instruments and sold under part number TSL 260R. The IR detector 111 can detect IR radiation over the wavelength range $8.0 \times 10^{-7}$ m (800 nm) to $1.1 \times 10^{-6}$ m (1100 nm), with peak sensitivity at $9.4 \times 10^{-7}$ m (940 nm). The central portion 106 comprises a cup made from rubber plastics material so as to be deformable against the surface of an egg. Power input and signal output leads for the IR sources 107, 108, 109 and 110, and the IR detector 111, are housed in a supply tube 112. Respective power supply and signal leads are housed in each of the arms 102, 103, 104 and 105.

Figure 16:
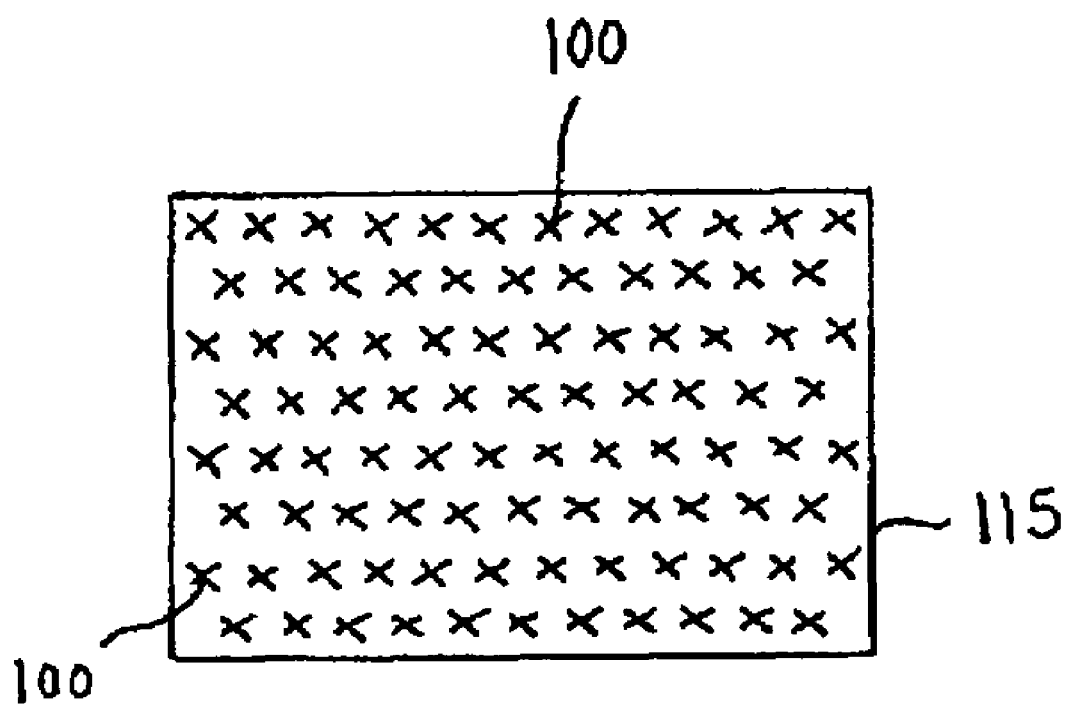
FIG. 16 is an underneath schematic plan view of a mount on which a plurality of the apparatus shown in FIG. 14 are mounted for testing the viability of eggs on a tray ("flat") or part of a tray of eggs, prior to injection and/or gender sorting of the eggs.

Referring to FIG. 16 a plurality of apparatuses 100 are mounted on an apparatus mount 115 comprising a metal frame that can be lowered and raised to bring each apparatus 100 onto and away from an egg in a flat of eggs (not shown) for simultaneous testing of the viability of the eggs. After testing the flat may be moved to an egg sorter (not shown) where the results of the testing process can be used to remove those eggs that are determined to be viable from the flat. Those eggs removed from the flat can then be inoculated, using the INOVOJECT® automated injection device (available from Embrex, Inc., Research Triangle Park, N.C., US), or sorted by gender, as in WO-A-98/14781 for example.

When the apparatus 100 is to be used, an egg 113 whose viability is to be determined is supported air-sac end up on a support 114 and brought under the apparatus 100. This apparatus is primarily designed for eggs of a developed stage e.g. 16, 17 and 18 days in poultry eggs (or at least approximately 50% into the incubation period), where the animal is too opaque to use transmission of light through the egg for heart detection. However, this apparatus is not exclusively useful for this purpose and will also work on younger eggs. The apparatus 100 is lowered onto the egg 113. It will be recalled that each arm 102, 103, 104 and 105 is biased downwardly to an equilibrium position. The equilibrium position is such that when the apparatus 100 is lowered onto the blunt air-sac end of the egg 113, each of the IR sources 107, 108, 109 and 110 contacts or is very close to the egg 113 and the arms are urged upwardly against the bias of the springs. In this way the apparatus 100 can accommodate eggs of different size and, via the independent pivoting of each arm, can receive an egg that is not centrally positioned with respect to the apparatus 100. As the apparatus 100 is further lowered onto the egg 113 the proximity sensor in the central portion 106 inhibits the apparatus from crushing the egg 113 and stops it in a position in which the cup is in abutment with the surface of the egg 113. This helps to reduce the effect of light reflected from the shell impinging directly onto the IR detector 111. The arms 102, 103, 104 and 105 can be fixed in position if preferred.

The IR sources 107, 108, 109 and 110, and the IR detector 111 are activated, using power from a mains source e.g. 240V at 50 Hz in the United Kingdom. 80 mA is supplied to each IR source, such that the radiant intensity incident on the shell of the egg is approximately 5 or 6 mW sr$^{-1}$ bearing in mind that each IR source is adjacent or abutting the shell of the egg (the power can be varied to supply incident radiation, at the shell of the egg, of radiant intensity between approximately 2-10 mW sr$^{-1}$ dependent on the saturation level of the amplifier in the sensing circuitry; the applicant has found that this produces good results with chicken eggs). Each infra-red source has a viewing half angle of 55° such that light is spread over a wide area. However, the incident intensity is such that if the emitter were placed at one end of the egg on its longitudinal axis and the detector placed at the opposite end, no light would be received by the detector due to absorption by the animal in the egg. In this way the chance of the animal being damaged by light of too high an intensity is reduced. Infra-red light passes from the sources 107, 108, 109 and 110 into the egg 113. Some of the light will be reflected from the surface of the egg and some will pass into it. The animal in the egg will absorb a proportion of the light that passes through the shell, particularly at the later stages of incubation as mentioned above when the animal is large and opaque. Some of the IR light will pass into the egg and into the air-sac 120 and impinge upon the allantois 121 or other blood carrying structures adjacent the air-sac. As described above, the allantois continually swells and contracts under action of the animal's heart. Accordingly, at some points during the heartbeat the allanto-chorion (or other vascular structure) will absorb more IR light and reflect less (when it is swollen with blood) and at other points in the cycle it will absorb less IR light and reflect more (when it has contracted). Some of the IR light is reflected back from the allanto-chorion in the direction of the IR detector 111. Due to the effect above, the IR light will have a time varying intensity representative of action of the animal's heart.

The cup around the IR detector 111 helps to inhibit sensing of IR light reflected from the shell of the egg 113, and to increase sensitivity to IR light emerging from within the egg 114. An output signal is obtained from the IR detector which is then processed as described in detail below.

The applicant has found that for determining the viability of eggs in the later stages of incubation, for example 16, 17 or 18 days in poultry eggs, the position of the IR detector with respect to the IR source can be of significant importance in obtaining satisfactory results. In particular, as mentioned above, a normally developed chick of such age is very opaque to any kind of light that is of an intensity that will not damage it, e.g. by overheating. In order to obtain good results the source and detector can be placed with respect to one another and an egg such that, either the IR light "glances" the egg, or is reflected from a vascular structure within the egg adjacent the inner surface of the shell. In the first case the IR source is positioned so as to direct light to pass through the shell, through a small part of the allanto-chorion (or other vascular structure) and out of the shell where the detector is positioned. In one arrangement this is performed near the air-sac end of the egg making positioning of the source and detector easier. In the second case, the emitter and detector are positioned to increase the chance of IR light reflected from the allanto-chorion (or other vascular structure) at the air-sac end of the egg being received by the detector. It is very unlikely that the air-sac will be symmetrical about the longitudinal axis of the egg, nor that the allantois (or other vascular structure from which infra-red may be reflected) will form angle of 90° to that axis. In particular, if, as is often the case, the allanto-chorion is pressed against the air-sac, it will form a substantially flat or slightly convex surface from which IR is reflected. The problem is that this surface often does not make an angle of 90° with the longitudinal axis of the egg. Furthermore it is not known at what angle around the longitudinal axis of the egg the surface is disposed. Thus, although the angle of incidence of infra-red onto the egg is known, it is not known what the angles of incidence onto and reflection from this surface are. Therefore it is not possible to know in advance where the strongest reflected component of infra-red light will be. By using light incident from a plurality of directions, the chances of the detector receiving a component of light reflected from this surface is increased. The plurality of directions may be obtained for example by using an emitter of wide viewing half angle (e.g. 55°) and/or a plurality of emitters disposed around the blunt end of the egg with a detector positioned on or adjacent the longitudinally axis of the egg. Alternatively, a plurality of detectors and an emitter may be used in the inverse arrangement. Referring to the close-up in FIG. 14 some of the light rays emitted by emitter 109 are shown schematically, in the way the applicant believes the invention to work. Some of the light passes into the animal in the egg and some is reflected, but not toward the detector 111. However, there is a part of the emitted infra red that is incident on the outer surface of the allanto-chorion at the right angle(s) such that at least part of it is diffusely reflected toward the detector 111, upon which intensity is modulated corresponding to action of the heart.

Accordingly there are some positions of source and sensor that will obtain a better output signal from the detector than others. To increase the chances of obtaining a good signal in a short time frame (e.g. 2s to 10s) there may be one or more IR sources and/or one or more IR detectors, for example like that described in connection with FIGS. 14 and 15. The applicant has found that a combination of four emitters disposed equi-circumferentially around the blunt end of the egg and a single detector on the longitudinal axis of the egg (as shown in FIGS. 14 and 15) has produced good results with chicken eggs of between 16 and 18 days into their incubation period. This arrangement mitigates the need to orientate the egg correctly with respect to the source and detector for the reasons given above. If for example a detector or source is positioned with its axis substantially in alignment with the longitudinal axis of the egg, corresponding source or detector can be placed between 0° and 90° with respect thereto, between 30° and 60° having given good results and 45° having given particularly good results with chicken eggs.

Figure 17:
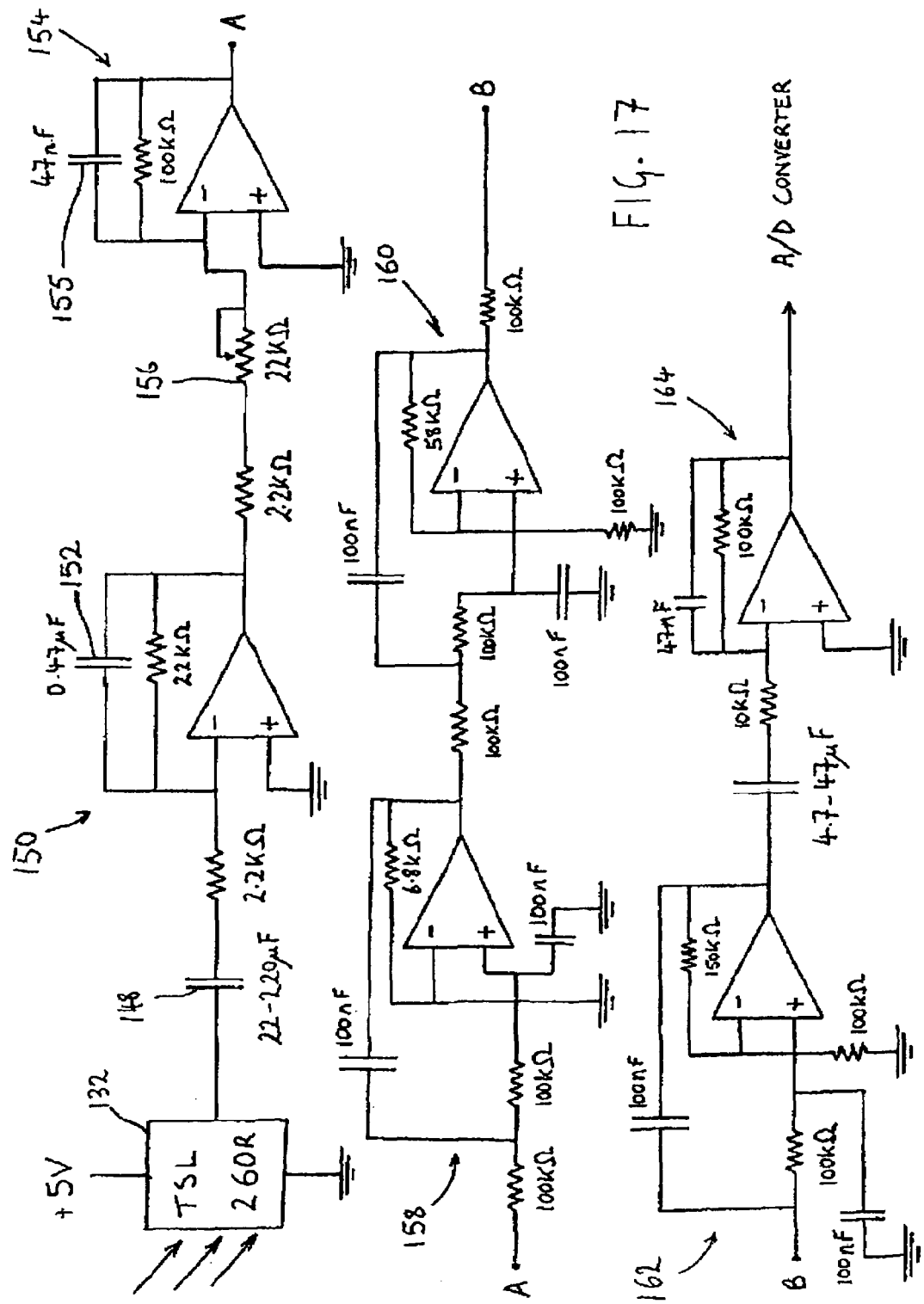
FIG. 17 is a circuit diagram of the amplification and filtering stages of the apparatus of FIG. 14.

The output from the IR detector 111 is processed in similar manner to that described in connection with FIG. 7. Referring to FIG. 17 signal amplifying and filtering circuitry for the apparatus 100 is shown. The circuitry in FIG. 17 is similar to the circuitry in FIG. 8 with like numerals indicating like parts. The output signal from the detector 111 is of the order of approximately 30 mV to 2.5V depending on the intensity of IR light sources, upon which the time varying voltage of the order of a few mV is superimposed as described above. It is this time varying signal that the circuitry is designed to extract and amplify. The output signal first passes through a capacitor 148 to extract the time varying part of the signal. The capacitor 148 may have a value of between approximately 22 µF to 220 µF. This is to control the settling time of the circuit i.e. the time is takes capacitor 148 to reach an equilibrium state in view of the signal generated by the relatively constant level of light received by the detector from the egg. If the capacitance is small the settling time (i.e. time constant) of the circuit is also small, 0.24 s in the case of 22 µF capacitor. If the capacitance is large the settling time is also large, 2.4 s in the case of a 220 µF capacitor. By varying the capacitance it is possible to control the settling time of the circuit for the particular application. However, by reducing the settling time of this part of the circuit there is a decrease in the circuit's low frequency response capability. If the response time is made too short, the circuit will attenuate the low frequency part of the signal caused by the heartbeat too heavily.

The time varying signal passes to a first gain stage 150 that applies a gain of 10 and also filters the signal with the capacitor 152. The capacitor 152 acts as a low pass filter with a filter corner frequency of 15 Hz i.e. the 15 Hz component of the input signal is reduced by 3 dB at this stage. 15 Hz corresponds to a heart rate of approximately 900 beats per minute, over which it is unlikely any animal's heart will beat, but also well below the 50 Hz (in the UK) signal generated by mains electricity (in the US: 60 Hz). The signal then passes to a second gain stage 54 that applies a gain of between 4.13 and 45.45,depending on the value of variable resistor 156 (variable between 0 and 22 kΩ). The signal is also filtered at stage 154, the capacitor 155 being a low pass filter with a filter corner frequency of 33 Hz i.e. the 33 Hz component of the input signal is reduced by 3 dB at this stage. Because of electrical interference in the wires generated for example by induction from mains power lines it is necessary to further filter the signal; if the signal is not further filtered the time varying signal corresponding to the variation in intensity of the received IR is likely to be totally drowned out by interference and noise. Accordingly, the signal then passes through a first filter stage 158 that applies a gain of 1.068, onto a second filter stage 160 that applies a gain of 1.58 and onto a third filter stage 162 that applies a gain of 2.50. Each filter stage is a low pass filter having a filter corner frequency set at 16 Hz i.e. the 16 Hz component of the input signal is reduced by 3 dB at each stage. Having been filtered, the signal passes through a final third gain stage 164 that applies a gain of 10 and a final low pass filtering of the signal with a corner frequency at 33 Hz. Accordingly the overall gain on the time varying signal is between 1742 and 19180 remembering that this is because of the variable resistor 156, and the signal has been filtered at 24 dB per octave (mainly due to the effect of filtering at stages 150, 158, 160 and 162). In this embodiment the variable resistor 156 is set to an overall gain of 1742. This gave a signal representative of the heart beat of a 16 day old bantam egg of 0.25V amplitude at 4 Hz. The signal then leaves this section of the apparatus and moves onto the analogue to digital converter.

It will be noted that in the amplifying and filtering circuit described above, the overall gain is set to minimum as opposed to maximum in the first embodiment. In the first embodiment the primary concern is to obtain an actual value for the heart rate which is extremely important when monitoring the incubation of rare and valuable animals, for example parrots. The heart rate can be used to infer whether the correct conditions exist around the egg for optimum incubation. However, when testing the viability of a large number of eggs per unit time, for example in commercial chicken farming, it is sufficient to know simply that the egg is viable. No accurate determination of heart rate is actually necessary. Accordingly, viability can be determined on the basis of ascertaining whether the signal from the IR detector 111 contains variation due to action of a heart or variation due to movement of the chick, the finding of either being sufficient to determine that the egg is viable. When an animal moves in an egg under test, the intensity of the IR light at the detector 111 varies from approximately 3 to 4 times up to 10 times more than the variation due to action of the heart. By reducing the gain of the amplifying stage it is possible to include the signal due to movement and the signal due to action of a heart on the same scale, and to detect both with appropriate algorithms.

Figure 18:
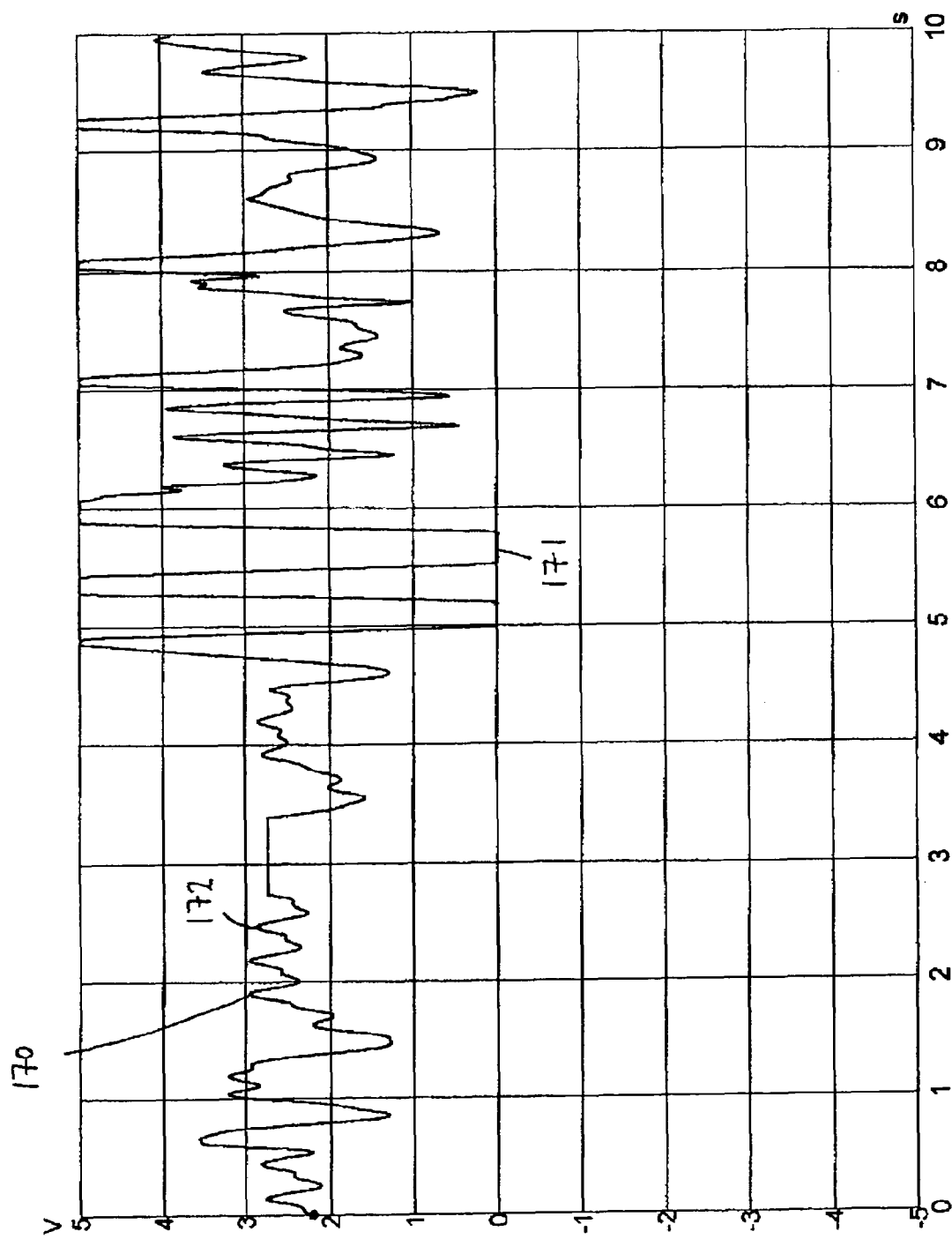
FIG. 18 is a trace of voltage (Y-axis) versus time (X-axis) for a day 19 bantam egg using the apparatus of FIG. 14.

Referring to FIG. 18 the voltage trace against time generated by a 19 day old bantam egg is shown; between approximately 1.75 s and 2.5 s the trace at 170 evidences the action of the heart. Between approximately 5 and 6 s the trace 171 shows that the chick has moved.

Figure 19:
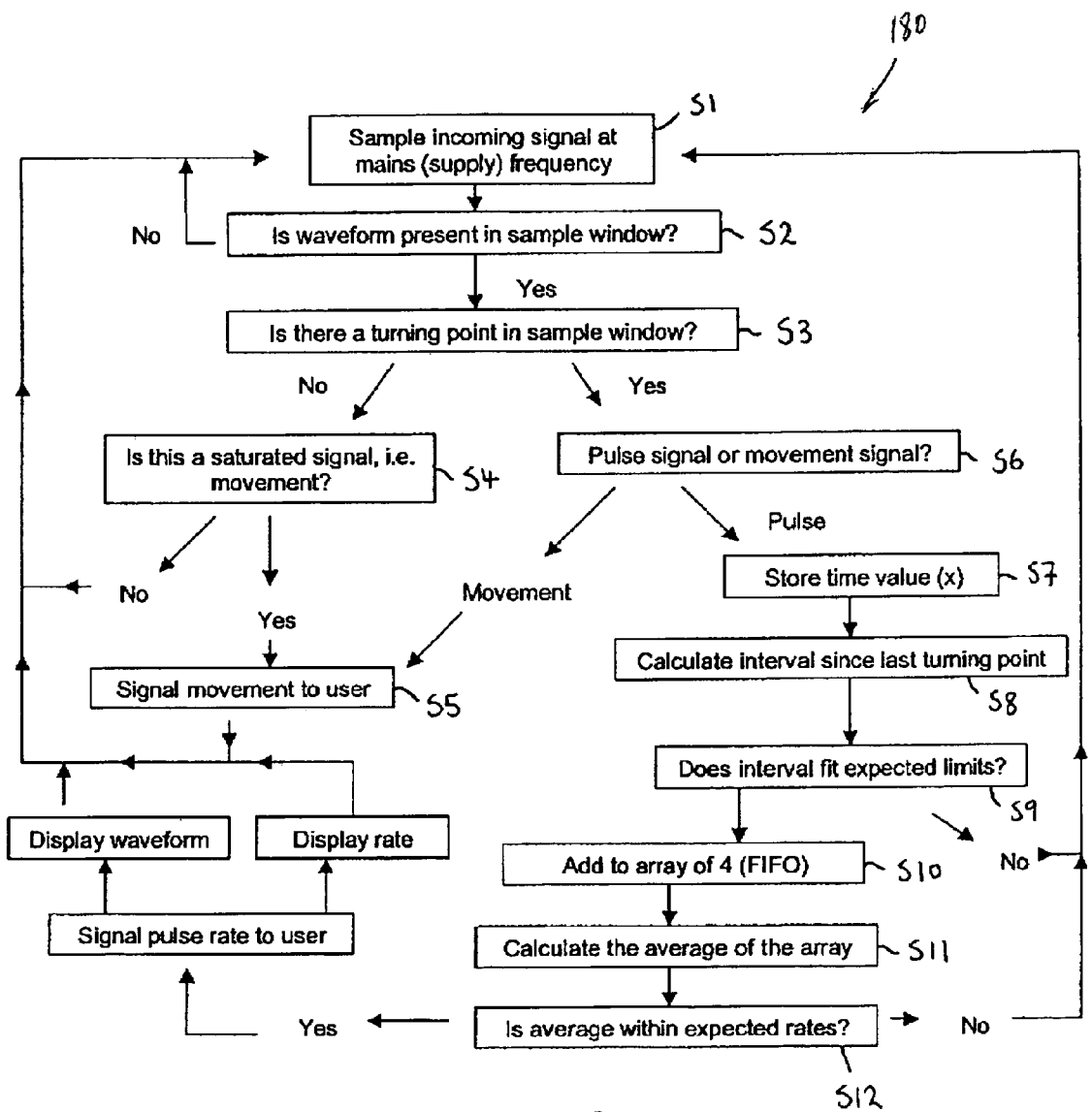
FIG. 19 is a flow diagram of the stages of a first embodiment of signal processing of the output from a detector of an apparatus in accordance with the present invention.

Referring to FIG. 19 the signal passes through a 10 bit analogue to digital (A/D) converter (not shown) that samples the signal at step S1 at 50 Hz which helps to eliminate any further interference by mains power induced since the amplifying and filtering circuit. The A/D converter samples the input voltage and assigns one of 1024 different values between 0V and 5V representative of the input signal at the sample time. The bit stream generated by the A/D converter is input into the microcontroller (not shown) where the signal is analysed. At step S2 the signal is analysed to determine whether or not it contains a wave form. Typically, at 16 to 18 days old a poultry egg will have a heartbeat of approximately 240 beats per minute i.e. 4 per second. This corresponds to eight "turning points" of the signal in one second. Accordingly one turning point should occur every 0.125 s. A "window" is applied to the incoming values of the signal; the window contains six values in time sequence from the A/D converter. The six values are placed into the window in reverse order so that value number 1 is the most recent sample in time. Since a sample is taken every 20 ms, this window represents 0.1 s of time of the signal from the detector 111 so that substantially an entire turning point can be seen in one window at the appropriate time. The microcontroller subtracts the sixth from the fifth value, the fifth and from the fourth value, the third from the second value, and the second from the first value to obtain four differences that are stored in a memory temporarily. The magnitude of each difference is compared to a minimum threshold difference, in this case 6 units on the A/D converter that corresponds to a rise of 33 mV. This is determined on the basis of the expected rise and fall of the signal due to a heart beat. If any of the differences are below the minimum threshold difference, then the microcontroller calculates the differences in reverse i.e. the fifth from the sixth value, the fourth from the fifth, the second from the third, and the first from the second. The magnitude of each difference is then compared to the minimum threshold difference. If neither of the two sets of differences meet this criteria the routine returns to step S1 and the next set of values are input into the window.

If at step S2, all of the values in the first set of differences exceed the minimum threshold (or if the first set does not, but the second set does), the routine proceeds to step S3 where the differences are retained in memory and used to determine whether or not the window contains a maximum turning point i.e. a part of the signal corresponding to the portion 172 of the trace in FIG. 18. This is done by examining the differences again. If there are two positive differences followed by two negative differences, then it is determined that the window contains a maximum turning point and the routine proceeds to step S6. However, if this condition is not satisfied, no turning point is found and the routine proceeds to step S4 where the microcontroller examines the values in the window again. If any of the values correspond to 0V or 5V then the microcontroller identifies movement and outputs a signal indicating that the egg is viable at step S5. If there are no values at these two extremes of the scale then the routine returns to step S1, slides the window along in time by one sample and the process is repeated.

Where the first set of differences does not meet the minimum threshold criteria but the second set does, step S3 is performed on the second set. However, the criteria to be met in this case are that there should be two negative differences followed by two positive differences. This will identify a minimum turning point i.e. part of the signal corresponding to the portion 173 of the trace in FIG. 18. If so, the routine proceeds to step S6.

In this way the algorithm identifies either a maximum turning point where the gradient of the signal changes from positive to negative, or a minimum turning point where the gradient of the signal changes from negative to positive.

At step S6 the routine compares a maximum threshold value against the differences calculated above. The maximum value is determined on the basis of differentiating between signal change due to movement and signal change due to heartbeat. As seen in FIG. 18 signal change due to movement will be readily determined on an amplitude basis. If the differences correspond to a voltage difference of more than a few tenths of a volt, then it can be assumed that the signal is due to movement and not heart rate. If so, the routine proceeds to step S5 and generates an output indicating that the egg is viable. If however, all of the differences are found to be below the maximum threshold value then the time at which value number 6 (i.e. the start of the turning point) was taken is stored in memory at step S7. Due to the criteria applied in step S3 above, this will only occur when substantially all of the maximum or minimum turning point is within the window. If, for example, there are two positive differences and one negative difference, or three negative differences, the condition in S3 will not be satisfied. The maximum error in determining the heart rate is at most 20 ms i.e. the time between samples. This corresponds to a ±2% error (note that this is not the error in determining viability, but the error in a numerical calculation of the heart rate, which in commercial farming is not needed). At step S8 the memory is examined for previously obtained turning point times to determine the time since the last maximum or minimum turning point and at step S9 it is determined whether this fits expected limits. However, since this is the first run through the routine there are no other values to use. Accordingly the time of this turning point is stored in memory. Assuming a uniform heart rate signal has been received as shown at 172 in FIG. 19 for example, the routine will need to run approximately six more times until the next turning point is central in the window. This corresponds to a time of 120 ms i.e. approximately 0.25 s. When the next turning point time is received the interval since the first turning point can be calculated at step S8 and, it the interval fits expected limits at step S9, the interval is stored in memory in an array of 4 values held in a first-in-first-out regime. As the egg is tested intervals are gradually stored in the FIFO memory until there are four at which point the routine proceeds to calculate the average of the array at step S11. If the average interval is within expected limits (see first embodiment described above) at step S12 then the microcontroller outputs a signal that the egg is viable. If not within expected limits the routine returns to S1 and the process is repeated.

Figure 20:
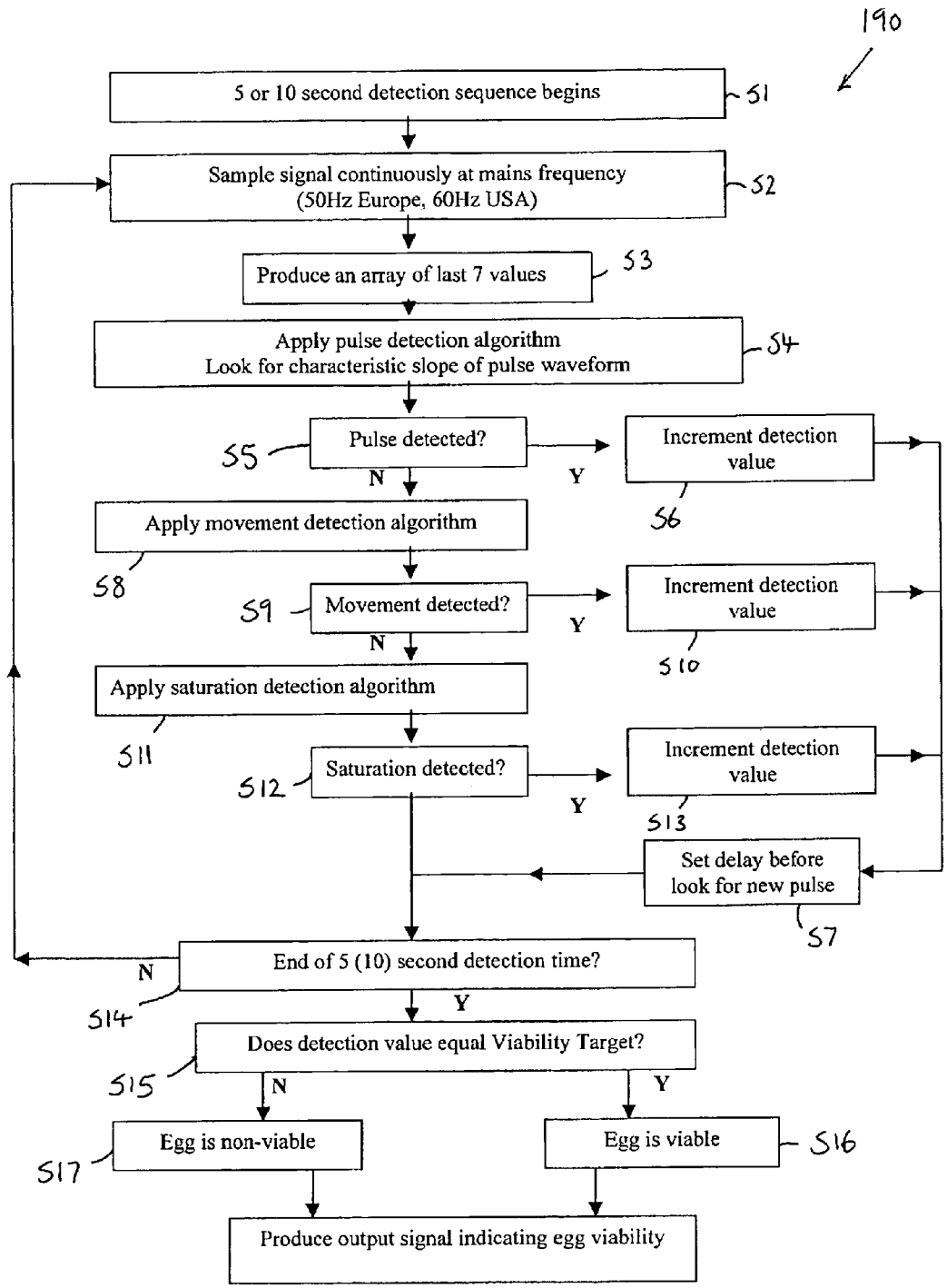
FIG. 20 is a flow diagram of the stages of a second embodiment of signal processing of the output from a detector of an apparatus in accordance with the present invention.
Figure 21:
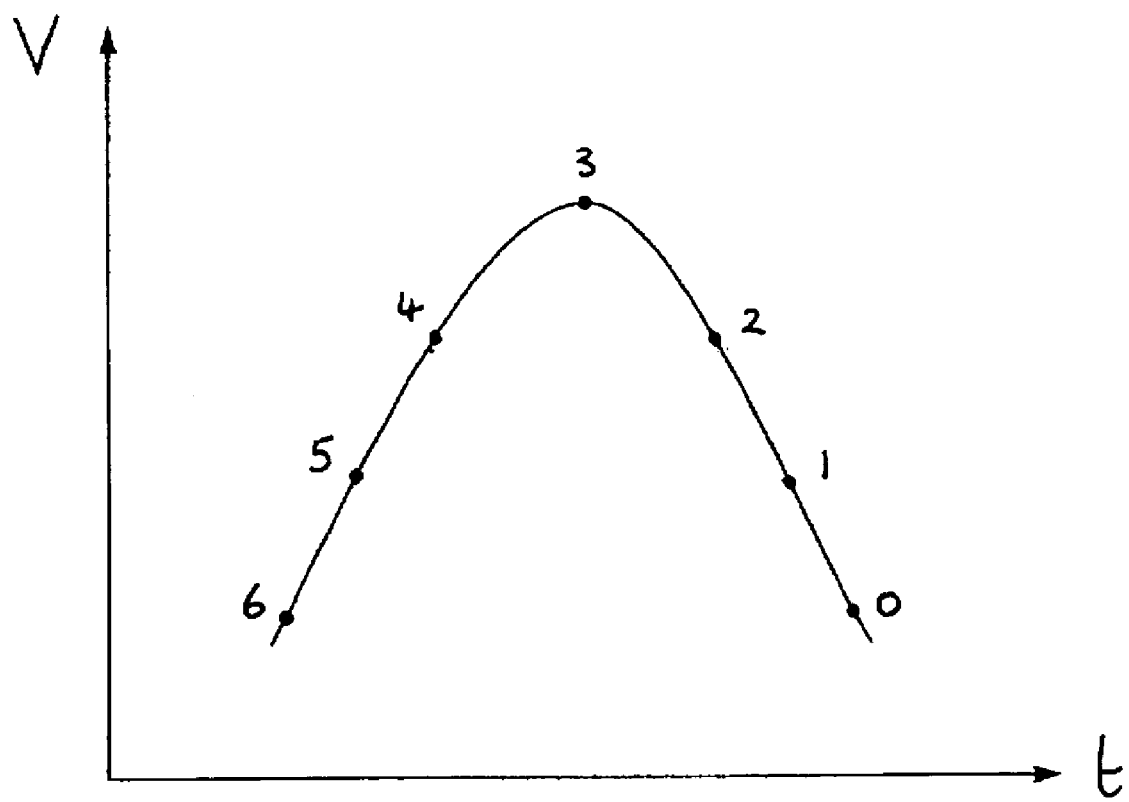
FIG. 21 is a schematic representation of the output signal corresponding to part of the cyclical variation in light intensity corresponding to action of a heart.

Referring to FIG. 20 a second embodiment of an algorithm for processing the signal is generally identified by reference numeral 190. The method begins by starting a timer at step S1 of 5 s during which the incoming signal will be analysed. The timer may be implemented using a clock signal from the microprocessor. An oscillating crystal in the microprocessor frequently generates such a signal. The signal passes through a 10 bit analogue to digital (A/D) converter (not shown) that samples the signal at step S2 at mains frequency (UK: 50 Hz; US: 60 Hz) which helps to eliminate any further interference by mains power induced since the amplifying and filtering circuit. The A/D converter samples the input voltage and assigns one of 1024 different values between 0V and 5V representative of the input signal at the sample time. The bit stream generated by the A/D converter is input into the microcontroller (not shown) where the signal is analysed. Typically, at 16 to 18 days old a poultry egg will have a heartbeat of approximately 180-240 beats per minute i.e. 3-4 per second. This corresponds to between six and eight "turning points" of the signal in one second. Accordingly one turning point should occur between approximately every 0.125 s and 0.167 s. At step S3 a "window" is applied to the incoming values of the signal; the window contains seven digital signal values, numbered 0 to 6,in time sequence from the A/D converter. The seven values are placed into the window in reverse order so that value number 0 is the most recent sample in time. Since a sample is taken every 20 ms (when sampled at 50 Hz), this window represents 0.12 s of time of the signal from the detector 111 so that substantially an entire turning point can be seen in one window at the appropriate time. FIG. 21 shows an idealised part of the signal upon which the seven values numbered 0 to 6 are shown to aid understanding.

The method then proceeds to step S4 in which a pulse detection algorithm is applied to the values in the window. Before doing this, a parameter herein called "detection value" is reset to zero. The detection value takes an integer value related to the viability of the egg as determined by the method. The significance of the detection value will be described in greater detail below. It will be noted from FIG. 18 that the pulse waveform comprises a jagged leading edge followed by a smooth trailing edge. The pulse detection algorithm is designed to look for the smooth peak part of the pulse, after the jagged portion on the leading edge. The pulse detection algorithm performs the following checks on the values in the window:

IF value 4–value 5>slope 2
AND value 1–value 0>slope 1
AND value 3>value 4
AND value 2>value 1 THEN
IF value 3–value 4<value 4–value 5
AND value 2–value 1<value 1–value 0 THEN pulse detected
GOTO STEP S6 and increment detection value by 1
OTHERWISE
IF value 5–value 4>slope 2
AND value 0–value 1>slope 1
AND value 4>value 3
AND value 1>value 2
THEN IF value 4–value 3<value 5–value 4
AND value 1–value 2<value 0–value 1
THEN pulse detected
GOTO step S6 and increment detection value by 1
OTHERWISE no pulse detected, proceed to step S8 where slope 1 and slope 2 are predetermined gradient values based on the expected slopes of a pulse waveform. Slope 1 corresponds to the expected gradient of the signal between value 6 and value 5, and slope 2 between value 5 and value 4. In this particular example, slope 1 has a value of 9 in digital bits that corresponds to an actual gradient of 2.2 mV ms$^{-1}$. Slope 2 has a value of 7 in digital bits that corresponds to 1.7 mV ms$^{-1}$. The digital values are dependent on the sampling rate of the signal and the number of bits used to assign the voltage value, in this case 50 Hz and 10 bits corresponding to 1024 digital bit values, respectively. These expected slope values in mV ms$^{-1}$ can be determined by trial and error and are greatly influenced by the filters in the circuitry. The circuitry described above filters the waveform at 24 dB per octave that results in a pulse waveform of a relatively rounded nature. If the signal was filtered less than this, the resulting pulse waveform would be sharper and the slope values needed would be higher. The applicant has found that filtering at 24 dB per octave produces a good balance between the frequency response of the circuit to the pulse waveform and reduction of noise, and it is this filtering value that the slope values above are based on.

As the expected signal is approximately symmetrical, the value of slope 1 also corresponds to the gradient of the signal between value 0 and value 1, and the value of slope 2 corresponds to the gradient between value 1 and value 2, albeit of opposite sign. However, as a result of the way in which the signal values are compared as set out above, the sign of the gradient is unimportant and therefore can be ignored. Furthermore, since the period of time between each sample is the same, the subtraction of two voltage values (y-axis) gives another voltage value representative of gradient of the signal between the two values; the time value of each sample is irrelevant and does not need to be taken in to account of the purposes of determining gradient.

Essentially, the pulse detection algorithm checks the data in the window by looking for an expected shape; the applicant has found that this improves the reliability of the final result. The test can be summarised as follows for a positive pulse:

(a) is there a gradient between values 5 and 6 of a magnitude bigger than a predetermined value?
(b) is there a gradient between values 1 and 0 of a magnitude bigger than a predetermined value?
(c) is value 3 the peak value in the window?
(d) is the gradient of the signal adjacent either side of the peak less than the gradient of the signal one sample further away?

Only when all of these conditions are satisfied does the method conclude that a positive pulse waveform has been detected.

It will be appreciated that the first half of the pulse detection algorithm checks for a positive pulse, similar to that shown in FIG. 21, whereas the second half checks for a negative pulse. If either a positive or a negative pulse is found, the algorithm increments the detection parameter by one at step S6, the new value being stored in memory. Furthermore the algorithm then proceeds to step S7 where a time delay is applied in the testing. If a pulse has been found, another pulse will not be expected for another 0.12 seconds or so depending on the heart rate of the animal in the egg. Accordingly, there is no point performing the pulse detection algorithm on data where there is expected to be no pulse i.e. approximately 5 windows of data. Thus this delay should be of the order of approximately 0.1 s corresponding to 5 windows of data. Once the delay has expired the method returns to step S2 and the process is repeated.

If the pulse detection algorithm has not found any evidence of a pulse, the method of FIG. 20 proceeds to step S8 where a movement detection algorithm is applied to the window of samples. Movement of the animal is characterised by voltage changes of a very steep positive or negative gradient, and by saturation of the amplifiers and therefore a maximum (or minimum) signal level. Heart rate will be superimposed upon these steeply rising or falling signals. However, the pulse detection algorithm described above will not locate them as they will appear "skewed" and therefore the above pulse detection tests not satisfied. Accordingly the aim of the movement detection algorithm is to find these steeply rising or falling signals within the window, that can be done at step S9 as follows:

IF value 5>(value 6+slope 1a)
AND IF value 4>(value 5+slope 2a)
AND IF value 2>(value 1+slope 2a)
AND IF value 1>(value 0+slope 1a)
THEN signal corresponds to movement (positive or negative gradient)
GOTO to step S10 and increment detection value by one
OTHERWISE no movement detected, proceed to step S11 where slope 1a and slope 2a are slope 1 and slope 2 each multiplied by a "pulse-movement ratio" factor respectively, in this case 3. Accordingly in this particular example slope 1a has a value of 27 digital bits or 6.6 mV ms$^{-1}$. The slope 2a has a value of 21 digital bits or 5.1 mV ms$^{-1}$. It has been found that movement signals generate gradients of at least three times the expected gradient for a pulse signal and thus this presents a suitable way of checking the signal for movement. It will be appreciated that the above checks will determine a positive gradient and a negative gradient, it being immaterial what the sign of the gradient is as explained above. Only the magnitude of the gradient is important. As explained above, if the frequency response of the filtering circuitry is adjusted, corresponding adjustment will need to be made of the values of slope 1a and 2a.

If the movement detection algorithm determines that the animal has moved, the detection parameter is incremented by one at step S10 and proceeds to step S7 as described above where a delay is applied. This is applied as a measure to prevent that same movement signal from continually incrementing the detection parameter. By waiting a short time and then repeating the process, the chances of a noise signal or other spurious signal leading to the conclusion that the egg is viable is reduced. Once the delay has expired the method returns to step S2 and the process is repeated.

If no movement is detected, the method proceeds to step S11 where a saturation detection algorithm is applied to the values in the window. The signal may become saturated i.e. have reached the maximum of 5V or a minimum of 0V and remain there for some time if the animal is moving. Thus the values in the window would all be approximately the same and the pulse detection algorithm and the movement detection algorithm would return a negative result i.e. that the egg is not viable. Accordingly the saturation detection algorithm checks at step S12 whether or not each of value 4, value 3, value 2, value 1 is greater than a predetermined value, in this case a value of 1010 on the 1024 scale (i.e. 10 bit), corresponding to nearly 5V; or whether or not each of value 4, value 3, value 2, value 1 is less than a predetermined value, in this case a bit value of 10 on the 1024 scale, corresponding to nearly 0V. If either of these conditions is met the saturation detection algorithm increments the detection value by one at step S13 and proceeds to step S7 where the time delay is applied. Again this is to reduce the chance of noise or other spurious signal resulting in a conclusion that the egg is viable. In this connection the applicant has noticed that noise, particularly vibration that is most common in commercial factories, tends to be characterised by short, sharp spikes in voltage lasting not more than approximately 20 ms duration. Thus by checking that there are consecutive samples greater than a predetermined level over a duration of 60 ms reduces the chances of a positive result resulting from noise.

At step S14 the algorithm determines whether or not the 5 s timer has expired. If it has not, it returns to step S2 and a new sample is generated from the signal for examination and the various steps described above repeated. Any additional increment of the detection value is added to that stored in memory from any previous run through the three life detection algorithms: pulse detection, movement detection and saturation. Thus the detection parameter is maintained and stored throughout the 5 s period and is only reset to zero at the very beginning. By monitoring the egg over a given time period and maintaining an electronic record of positive viability results within that time period, the accuracy of the method and apparatus is increased.

Once the timer has expired the algorithm proceeds to step S15 where it determines whether or not the stored value of the detection parameter is greater than or equal to a "viability target". The viability target is a value of the detection parameter that, over the 5 s time period of testing, the applicant has found gives reasonably certainty to viability of the egg under test. For example, for a 5 s test the applicant has found that if the detection parameter is 4 or more then the egg can be said with a good degree of confidence to be viable and this result is output at step S16. If, however, the detection parameter is 3 or less, the egg can be said with a good degree of confidence not to be viable and this result is output at step S17.

It is of course possible to test an egg over different detection times. If 10 seconds is used the detection parameter should be at least 7 to be reasonably confident that the egg is viable. The applicant has performed the test in 3 s; however, there is a trade off between test time and the level of confidence of the results. 5 s is preferred to provide a balance between the two. For example the applicant has tested 5000 commercial chicken eggs at day 18 of their 21 day incubation period using apparatus similar to that in FIG. 14 and processed the output signal in accordance with the method 190 described above. A correct determination of viability was made for 4999 of those eggs, the correct determination being verified by manual inspection of each egg.

Figure 6:
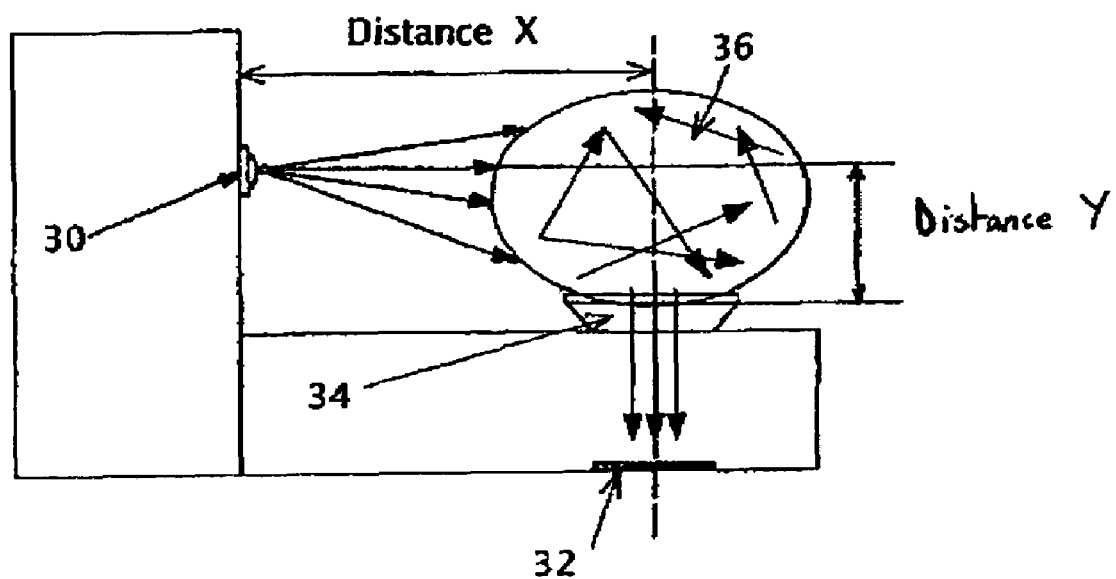
FIG. 6 is a schematic cross section through the apparatus of FIG. 3 in use determining the viability of an egg, part of the apparatus omitted for clarity.

Either of the aforementioned methods 180 and 190 can be used with the apparatus of FIG. 4-6.

When using a plurality of apparatus 100 on an apparatus mount 115 as shown in FIG. 16 for example, the method 180 or 190 described above is performed for each egg held in the flat. The results of the test may be stored electronically and forwarded to an egg sorter where those eggs that have been determined to be viable are removed. Those eggs may then be inoculated and/or sorted by gender, and finally placed in one or more hatching baskets for the final stages of incubation. During use the microprocessor may calculate the percentage of eggs that viable in a batch under test and this may be displayed to an operator or stored in memory.

Between testing one flat and another, the IR detectors of the or each apparatus 100 may be de-activated to inhibit saturation by background IR light from daylight or artificial lighting for example. Alternatively, shielding means may be provided around each apparatus or the apparatus mount 115 to reduce the effect of background IR light on the detectors. In this way, the time taken for the amplification and filtering circuitry to settle after the detector is moved adjacent an egg is reduced.

It is to be noted that for the second embodiment of the apparatus 100, shielding means around the egg for shielding against background IR is not essential. Where the first embodiment of the apparatus is mains powered and sufficient power is available to power the IR source at a higher intensity and to power the lower sensitivity (in terms of signal generated per unit of light falling thereon) detector, the shielding means in this embodiment is not essential.

Instead of the four arms 102, 103, 104, 105, the infra-red light sources may be mounted on the rim of a standard suction cup that is mounted on the supply tube 112. Alternatively, the infra-red light sources may be mounted within recesses formed in the suction cup. The recesses should be of the appropriate dimensions to ensure that the infra-red light sources substantially abut or are very close to the surface of the shell in use. In whatever arrangement is used it is important that the infra-red detector is shielded as far as possible from a direct line of sight component from the emitters. The use of the suction cup with the infra-red emitters abutting or very close to the shell of the egg has the additional advantage that wide viewing angle sources (e.g. greater than 90°) can be used whilst the risk of a direct line of sight component reaching the infra-red detector is reduced. Use of a wide viewing angle source increases the range of angles that infra-red is incident (from a single source) on the allanto-chorion adjacent the air-sac, thereby increasing the chance of receiving a reflected component at the detector. In this way the accuracy and reliability of the apparatus is enhanced and the applicant has obtained the aforementioned results with such an arrangement.

Such a suction cup with IR sources mounted thereon may also be used in the apparatus shown in FIGS. 3-6. The suction cup can be placed in an upright position so as to support an egg standing therein. The egg may be tested in this position, preferably with its blunt end in the suction cup. In this arrangement the need for an IR emitter on the side of the housing is mitigated.

The in ovo treatment referred to herein may use substances injected into an egg to achieve a desired result. Such substances may be vaccines, antibiotics, vitamins, virus and immunomodulatory substances for example. Vaccines designed for in ovo use to combat outbreaks of avian diseases in hatched birds are commercially available. Typically a substance is dispersed in a fluid medium, or a solid dissolved in a fluid, or a particulate dispersed or suspended in a fluid. Accordingly references herein to in ovo treatment refers to the placing of such a substance within an egg prior to hatch. The substance may be placed within an extra embryonic compartment of the egg (e.g. yolk sac, amnion, allantois) or within the embryo itself. The site into which injection is achieved will vary depending on the substance injected and the outcome desired.

The apparatus and methods herein may be used in the propagation of vaccines using poultry eggs. The live virus can be placed in live poultry eggs where it propagates. After a period of incubation, virus-rich parts of the egg can be harvested (e.g. chorioallantoic fluid) and used to make the vaccine. If the chick dies during incubation, harvesting the parts of the egg containing virus will also retrieve any bacteria that have infected the egg. Accordingly, it is desirable to test the viability of eggs prior to harvesting the virus to ensure that this does not happen. Viability can be determined using methods and apparatus described herein.

We claim:

1. A method of determining the viability of an egg, which method comprises the steps of:
   (a) causing electromagnetic radiation to impinge upon the egg, the electromagnetic radiation having one or more wavelengths in the infra-red part of the spectrum;
   (b) receiving at least a part of the infra-red radiation that has passed through the egg and generating an output signal representative of the received infra-red radiation;
   (c) processing said output signal to determine whether there is a cyclical variation in the intensity of the infra-red radiation leaving the egg corresponding to action of a heart, the existence of said cyclical variation indicating that the egg is viable; and
   (d) providing an output result of the viability of the egg as determined by step (c);
   wherein step (a) is performed by directing infra-red radiation so that it passes through the shell for reflection from the allanto-chorion adjacent an inner surface of said shell, and step (b) is performed by receiving any infra-red radiation so reflected.

2. A method as claimed in claim 1, further comprising the step of using infra-red radiation of an intensity incident on the egg such that if radiation is caused to impinge on one end of the egg, zero or substantially zero radiation would be received at the opposite end of the egg.

3. A method as claimed in claim 2, wherein the infra-red radiation has a radiant intensity incident on the egg of between approximately 2 and 10 mW sr$^{-1}$, and preferably between approximately 4 and 6 mW sr$^{-1}$.

4. A method as claimed in claim 1, wherein step (b) is performed by receiving reflected infra-red radiation in a position out of direct line of sight of the direction which infra-red radiation enters the egg.

5. A method as claimed in claim 1, wherein step (a) is performed by directing infra-red radiation at the air-sac inside the egg from a position adjacent the blunt end thereof.

6. A method as claimed in claim 1, wherein step (a) is performed by directing infra-red radiation at the egg from a plurality of directions.

7. A method as claimed in claim 1, further comprising the step of receiving infra-red radiation in a position substantially co-axial with the longitudinal axis of the egg and at the blunt end thereof.

8. A method as claimed in claim 1, further comprising the step of electronically examining a portion of said output signal for a waveform with a shape similar to an expected shape resulting from said cyclical variation and/or movement of the animal in the egg.

9. A method as claimed in claim 8, further comprising the step of electronically determining whether or not a part of said portion has a gradient greater than a first minimum threshold for that part, said first minimum threshold set according to the expected gradient if said portion contains said cyclical variation.

10. A method as claimed in claim 8, wherein said cyclical variation as represented by said output signal comprises a jagged leading edge, a turning point and a substantially smooth trailing edge, the method further comprising the step of electronically examining said portion for that part of the cyclical variation beyond the jagged part of the leading edge and comprising the turning point and at least part of the substantially smooth trailing edge.

11. A method as claimed in claim 8, further comprising the step of electronically examining said portion to determine whether or not a turning point is present therein.

12. A method as claimed in claim 11, further comprising the step of, when a turning point is present, electronically examining said portion to determine whether or not the gradient of a first part of said portion is less than the gradient of a second part of said portion, said first part being nearer to said turning point than said second part.

13. A method as claimed in claim 8, further comprising the step of electronically determining whether or not a part of said portion has a gradient greater than a second minimum threshold for that part, said second minimum threshold set according to the expected gradient if said portion contains a signal representing movement of the animal, such a movement signal being characterised by a rising and/or falling signal of a gradient steeper than results from said cyclical variation.

14. A method as claimed in claim 13, wherein said second minimum threshold is set as a multiple of the expected gradient of part of said portion if it contains said cyclical variation.

15. A method as claimed in claim 8, further comprising the step of electronically examining said portion for a part of a substantially constant level, said substantially constant level being representative of movement of the animal in the egg.

16. A method as claimed in claim 15, wherein said substantially constant level is at or near maximum or minimum output signal level.

17. A method as claimed in claim 8, further comprising the steps of electronically storing a detection value parameter and, upon detection of said cyclical variation or movement, adjusting said detection value parameter as a record of said detection.

18. A method as claimed in claim 17, further comprising the step of, upon detection of said cyclical variation or movement, repeating the steps of claim 10 on a different portion of said output signal.

19. A method as claimed in claim 18, further comprising the step of electronically examining said output signal for a predetermined time and at the end thereof, electronically comparing said detection value parameter against a predetermined threshold, said predetermined threshold being a minimum value of the detection value parameter that indicates said egg is viable over the predetermined time.

20. A method as claimed in claim 18, further comprising the step of, upon detection of said cyclical variation or movement, implementing a delay before examining said different portion.

21. A method as claimed in claim 20, wherein the magnitude of said delay is based upon the time difference between consecutive cyclical variations.

22. A method as claimed in claim 1, further comprising the step of receiving an infra-red radiation wavelength range between more than $7.5 \times 10^{-7}$ m and $1.0 \times 10^{-3}$ m.

23. A method as claimed in claim 22, wherein said range is between approximately $8.0 \times 10^{-7}$ m and $1.1 \times 10^{-6}$ m.

24. A method as claimed in claim 22, further comprising the step of receiving a wavelength in said range with a maximum sensitivity, said wavelength being approximately $9.4 \times 10^{-7}$ m or greater.

25. A method as claimed in claim 1, further comprising the step of performing the method on a plurality of eggs substantially simultaneously.

26. A method as claimed in claim 25, further comprising the steps of generating a signal representative of the viability of each egg of the plurality of eggs, forwarding said signal to a mechanical sorter, and using said signal to control said sorter to remove those eggs from the plurality of eggs that were determined to be viable.

27. A method as claimed in claim 1, wherein the or each egg is a poultry egg of 16, 17 or 18 days into its incubation period.

28. A method of vaccinating eggs in ovo, for example poultry eggs, which method comprises the steps of:
 (a) determining the viability of a plurality of eggs using a method as claimed in claim 1;
 (b) removing those eggs determined to be viable in step (a) from the plurality of eggs; and
 (c) vaccinating the viable eggs in ovo.

29. A method of sorting eggs, for example poultry eggs, by gender, which method comprises the steps of:
 (a) determining the viability of a plurality of eggs using a method as claimed in claim 1;
 (b) removing those eggs determined to be viable in step (a) from the plurality of eggs; and
 (c) sorting the viable eggs by gender.

30. An apparatus for determining the viability of an egg, which apparatus comprises an emitter for causing electromagnetic radiation to impinge upon an egg, the electromagnetic radiation having one or more wavelengths in the infra-red part of the spectrum, a receiver for receiving at least a part of the infra-red radiation that has passed through the egg and generating an output signal representative of the received infra-red radiation, and a processor for processing said output signal to determine whether there is a cyclical variation in the intensity of the infra-red radiation leaving the egg corresponding to action of a heart, the existence of said cyclical variation indicating that the egg is viable,
 the arrangement being such that, in use, said emitter is positioned to direct infra-red radiation so that it passes through the shell for reflection from an outer surface of a vascular structure adjacent an inner surface of said shell and said receiver is positioned to receive any infra-red radiation so reflected.

31. An apparatus for determining the viability of a plurality of eggs, which apparatus comprises a plurality of apparatus as claimed in claim 30, a tray for holding a plurality of eggs adjacent said plurality of apparatus, a carrier movable into and out of engagement with the plurality of eggs and a circuit for generating an output signal indicative of those eggs that are viable and/or those eggs that are not viable.

32. An apparatus for sorting a plurality of eggs by viability, which apparatus comprises a holder for receiving a tray of eggs whose viability has been determined, a circuit for receiving a signal from an apparatus as claimed in claim 31 indicative of those eggs that are viable and/or not viable, and a remover for removing either the viable eggs or the non-viable eggs from the plurality of eggs.

33. A computer program comprising computer executable process steps for performing a method in accordance with claim 8.

34. A computer program as claimed in claim 33, embodied on a record medium, stored in a computer memory, embodied in a read-only memory or carried on an electrical signal carrier.

35. A method of producing chickens, which method comprises the steps of:
 (1) incubating a plurality of eggs;
 (2) testing the viability of each egg of the plurality of eggs anywhere between approximately 16 and 18 days into their 21 day incubation period;
 (3) inoculating those eggs determined to be viable; and
 (4) further incubating the inoculated eggs to hatch;
 wherein the viability test is carried out by the method of claim 1.

36. A method of propagating a vaccine, which method comprises the steps of:
 (1) placing a live virus in a plurality of eggs;
 (2) incubating the plurality eggs;
 (3) testing the viability of each egg of the plurality of eggs; and
 (4) harvesting virus-rich parts of those eggs determined to be viable;
 wherein the viability test is carried out by the method of claim 1.

* * * * *